United States Patent [19]
Olivera et al.

[11] Patent Number: 5,591,821
[45] Date of Patent: Jan. 7, 1997

[54] OMEGA-CONOTOXIN PEPTIDES

[75] Inventors: Baldomero M. Olivera; David R. Hillyard; Julita S. Imperial, all of Salt Lake City, Utah; Virginia D. Monje, Quezon City, Philippines

[73] Assignee: The University of Utah, Salt Lake City, Utah

[21] Appl. No.: 92,215

[22] Filed: Jul. 16, 1993

[51] Int. Cl.$^6$ ............................ C07K 14/00; C07K 7/00; A61K 38/00
[52] U.S. Cl. ............................................................ 530/324
[58] Field of Search .................. 514/12, 13; 530/324, 530/327

[56] References Cited

U.S. PATENT DOCUMENTS

| | | |
|---|---|---|
| 4,447,356 | 5/1984 | Olivera et al. . |
| 4,562,175 | 12/1985 | Chang et al. ............................. 514/12 |
| 5,051,403 | 9/1991 | Miljanich et al. . |

FOREIGN PATENT DOCUMENTS

| | | |
|---|---|---|
| 9310145 | 5/1993 | WIPO . |
| 9313128 | 7/1993 | WIPO . |

OTHER PUBLICATIONS

Monje, et al, Neuropharmacology vol. 32, No. 11, pp. 1141–1149, 1993.
Olivera, et al, *J. Biol. Chem.,* 266(33), 22067–71.
Olivera, et al, *Biochemistry,* 26, 2086–2090, 1987.
McIntosh, M. et al. (1982). Isolation and Structure of a Peptide Toxin from the Marine Snail Conus magus. Arch. Biochem. Biophys. 218: 329–334.
Olivera, B. M. et al. (1984). Purification and Sequence of a Presynaptic Peptide Toxin from Conus geographus Venom. Biochemistry 23:5087–5090.
Olivera, B. M. et al. (1985). Peptide Neurotoxins from Fish–Hunting Cone Snails. Science 230: 1338–1343.
Cruz, L. J. et al. (1986). Calcium Channel Antagonists. *J. Biol. Chem.* 261:6230–6233.
McCleskey, E. W. et al. (1987). w–Conotoxin: Direct and Persistent Blockade of Specific Types of Calcium Channels in Neurons But Not Muscle. Proc. Natl. *Acad. Sci. USA* 84:4327–4331.
Olivera, B. M. et al. (1987). Neuronal Calcium Channel Antagonists. Discrimination Between Calcium Channel Subtypes Using w–Conotoxin from Conus magus Venom. Biochemistry 26: 2086–2090.
Rivier, J. P. et al. (1987). Neuronal Calcium Channel Inhibitors. *J. Biol. Chem.* 262:1194–1198.
Yoshikami, D. et al. (1989). The Inhibitory Effects of Omega–Conotoxins on Ca Channels and Synapses. Ann. NY Acad. Sci. 560:230–248.
Olivera, B. M. et al. (1990). Diversity of Conus Neoropeptides. *Science* 249:257–263.
Olivera, B. M. et al. (1991). Conotoxins. *J. Biol. Chem.* 266:22067–22070.
Lundy, P. M. et al. (1991). Pharmacological evidence for an w–conotoxin, dihydropyridine–insensitive neuronal $Ca^{2+}$ channel. Eur. J. Pharmacol. 206: 61–68.
Regan, L. J. et al. (1991). $Ca^{2+}$ Channels in Rat Central and Peripheral Neurons: High–Threshold Current Resistant to Dihydropyridine Blockers and w–Conotoxin. *Neuron* 9:69–77.
Hillyard, D. R. et al. (1992). A New Conus Peptide Ligand for Mammalian Presynaptic $Ca^{2+}$ Channels. *Neuron* 9:69–77.
Ramilo, C. A. et al. (1992). Novel a—and w–Conotoxins from Conus striatus Venom. Biochemistry 31:9919–9926.

*Primary Examiner*—Elizabeth C. Weimar
*Assistant Examiner*—S. G. Marshall
*Attorney, Agent, or Firm*—Venable, Baetjer, Howard & Civiletti, LLP

[57] ABSTRACT

The present invention is directed to ω-conotoxin peptides having 24–30 amino acids, six cysteines which form disulfide bonds between the first and fourth, second and fifth, and third and sixth cysteines, respectively, and an internal sequence of Cys-Arg-Lys-Thr-$Xaa_1$-Tyr-$Xaa_2$-Cys-Cys-Ser-Gly-Ser-Cys (SEQ ID NO:1). The invention is further directed to ω-conotoxin peptides of the generic formula Cys-$Xaa_1$-Gly-$Xaa_2$-Gly-Ala-$Xaa_3$-Cys-Arg-Lys-Thr-$Xaa_4$-Tyr-$Xaa_5$-Cys-Cys-Ser-Gly-Ser-Cys-$Xaa_6$-Arg-Gly-$Xaa_7$-Cys (SEQ ID NO:2). Preferably, the C-terminus is amidated. These peptides also contain three disulfide bonds. Examples of ω-conotoxin peptides within the generic formula are MVIIC having the formula Cys-Cys-Gly-Lys-Gly-Ala-$Xaa_1$-Cys-Arg-Lys-Thr-$Xaa_2$-Tyr-Asp-Cys-Cys-Ser-Gly-Ser-Cys-Gly-Arg-Arg-Gly-Lys-Cys (SEQ ID NO:3), wherein Xaa is preferably Pro or Hyp (4-hydroxyproline) and $Xaa_2$ is preferably Met or Nle (norleucine) and wherein preferably the C-terminus is amidated, and MVIID having the formula Cys-Gln-Gly-Arg-Gly-Ala-Ser-Cys-Arg-Lys-Thr-Xaa-Tyr-Asn-Cys-Cys-Ser-Gly-Ser-Cys-Asn-Arg-Gly-Arg-Cys (SEQ ID NO:4), wherein Xaa is preferably Met or Nle (norleucine), and wherein preferably the C-terminus is amidated. These peptides target the P-like subtypes of $Ca^{2+}$ channels as well as the N-type $Ca^{2+}$ channels.

20 Claims, 3 Drawing Sheets

OMEGA-CONOTOXIN PEPTIDES

This invention was made with Government support under Grant No. GM-22737 awarded by the National Institutes of Health, Bethesda, Md. The United States Government has certain rights in the invention.

BACKGROUND OF THE INVENTION

This invention relates to relatively short peptides, and more particularly to peptides between about 24 and about 30 residues in length, which are naturally available in minute amounts in the venom of the cone snails or analogous to the naturally available peptides, and which include three cyclizing disulfide linkages.

The publications and other materials used herein to illuminate the background of the invention, and in particular, cases to provide additional details respecting the practice, are incorporated by reference, and for convenience are numerically referenced in the following text and respectively grouped in the appended bibliography.

Mollusks of the genus Conus produce a highly toxic venom which enables them to carry out their unique predatory lifestyle. Prey are immobilized by the venom which is injected by means of a highly specialized venom apparatus, a disposable hollow tooth which functions both in the manner of a harpoon and a hypodermic needle.

Few interactions between organisms are more striking than those between a venomous animal and its envenomated victim. Venom may be used as a primary weapon to capture prey or as a defense mechanism. These venoms disrupt essential organ systems in the envenomated animal, and many of these venoms contain molecules directed to receptors and ion channels of neuromuscular systems.

The predatory cone snails (Conus) have developed a unique biological strategy. Their venom contains relatively small peptides that are targeted to various neuromuscular receptors and may be equivalent in their pharmacological diversity to the alkaloids of plants or secondary metabolites of microorganisms. Many of these peptides are among the smallest nucleic acid-encoded translation products having defined conformations, and as such, they are somewhat unusual. Peptides in this size range normally equilibrate among many conformations. Proteins having a fixed conformation are generally much larger.

The cone snails that produce these toxic peptides, which are generally referred to as conotoxins or conotoxin peptides, are a large genus of venomous gastropods comprising approximately 500 species. All cone snail species are predators that inject venom to capture prey, and the spectrum of animals that the genus as a whole can envenomate is broad. A wide variety of hunting strategies are used; however, every Conus species uses fundamentally the same basic pattern of envenomation.

The major paralytic peptides in these fish-hunting cone venoms were the first to be identified and characterized. In C. geographus venom, three classes of disulfide-rich peptides were found: the α-conotoxin peptides (which target and block the nicotinic acetylcholine receptors); the μ-conotoxin peptides (which target and block the skeletal muscle $Na^+$ channels); and the ω-conotoxin peptides (which target and block the presynaptic neuronal $Ca^{2+}$ channels). However, there are multiple homologs in each toxin class; for example, there are at least five different ω-conotoxin peptides present in C. geographus venom alone. Considerable variation in sequence is evident, and when different ω-conotoxin peptide sequences were first compared, only the cysteine residues that are involved in disulfide bonding and one glycine residue were found to be invariant. Another class of conotoxins found in C. geographus venom is that referred to as conantokins, which cause sleep in young mice and hyperactivity in older mice and are targeted to the NMDA receptor. Each cone venom appears to have its own distinctive group, or signature, of different conotoxin sequences.

Many of these peptides have now become fairly standard research tools in neuroscience. μ-Conotoxin peptides, because of their ability to preferentially block muscle but not axonal $Na^+$ channels, are convenient tools for immobilizing skeletal muscle without affecting axonal or synaptic events. ω-Conotoxin peptides have become standard pharmacological reagents for investigating voltage-sensitive $Ca^{2+}$ channels and are used to block presynaptic termini and neurotransmitter release.

The most widely used pharmacological agent for inhibiting neurotransmitter release at the present time is a peptide, ω-conotoxin peptide GVIA, which was isolated from the venom of the predatory fish-hunting snail, C. geographus (1, 2). This peptide binds with very high affinity and specificity to presynaptic voltage-sensitive $Ca^{2+}$ channels (2, 3). In synaptic systems from lower vertebrates, the toxin has proven to be a generally potent agent for inhibiting neurotransmitter release. Thus, if the entry of $^{45}Ca^{2+}$ is monitored in response to depolarization using synaptosomal preparations from frog or chick brain, the inhibition of $Ca^{2+}$ entry by the peptide is essentially complete (10).

In mammalian systems, ω-conotoxin peptide GVIA is apparently effective on a much more restricted subset of $Ca^{2+}$ channels. Thus, while the peptide causes paralysis in teleost, amphibian and avian systems, the toxin has no measurable effect on most mammalian neuromuscular junctions, even at very high doses (4). In addition, the toxin inhibits only a minor fraction of the total depolarization-induced $^{45}Ca^{2+}$ influx in most rat brain synaptosome preparations (5). These results indicate that at mammalian synapses, there are critically important voltage-sensitive $Ca^{2+}$ channels that under physiological conditions are insensitive to ω-conotoxin peptide GVIA. It is therefore necessary to develop other ligands in order to study synaptic transmission in mammalian systems.

Every piscivorous Conus species that has been analyzed so far has at least two divergent ω-conotoxin peptide sequences, and homologous toxins from venoms of different Conus species exhibit surprising sequence divergence. From the fish-hunting species C. magus, a highly variable Indo-Pacific species, two ω-conotoxin peptides were previously described—MVIIA and MVIIB (6, 7).

ω-Conotoxin peptide MVIIA has high affinity for the ω-conotoxin peptide GVIA high affinity site, the N-type $Ca^{2+}$ channel. It is desired to identify and synthesize ω-conotoxin peptides which do not primarily target to N-channels in mammalian systems.

SUMMARY OF THE INVENTION

The present invention is directed to ω-conotoxin peptides having 24–30 amino acids, six cysteines which form disulfide bonds between the first and fourth, second and fifth, and third and sixth cysteines, respectively, and an internal sequence of Cys-Arg-Lys-Thr-$Xaa_1$-Tyr-$Xaa_2$-Cys-Cys-Ser-Gly-Ser-Cys (SEQ ID NO:1). The invention is further directed to ω-conotoxin peptides of the generic formula Cys-$Xaa_1$-Gly-$Xaa_2$-Gly-Ala-$Xaa_3$-Cys-Arg-Lys-Thr-$Xaa_4$-

Tyr-Xaa$_5$-Cys-Cys-Ser-Gly-Ser-Cys-Xaa$_6$-Arg-Gly-Xaa$_7$-Cys (SEQ ID NO:2). Preferably, the C-terminus is amidated. These peptides also contain three disulfide bonds, as described above.

Examples of ω-conotoxin peptides within the generic formula are MVIIC having the formula Cys-Lys-Gly-Lys-Gly-Ala-Xaa$_1$-Cys-Arg-Lys-Thr-Xaa$_2$-Tyr-Asp-Cys-Cys-Ser-Gly-Ser-Cys-Gly-Arg-Arg-Gly-Lys-Cys (SEQ ID NO:3), wherein Xaa$_1$ is preferably Pro or Hyp (4-hydroxyproline) and Xaa$_2$ is preferably Met or Nle (norleucine), and wherein preferably the C-terminus is amidated, and MVIID having the formula Cys-Gln-Gly-Arg-Gly-Ala-Ser-Cys-Arg-Lys-Thr-Xaa-Tyr-Asn-Cys-Cys-Ser-Gly-Ser-Cys-Asn-Arg-Gly-Arg-Cys (SEQ ID NO:4), wherein Xaa is preferably Met, Ser or Nle (norleucine), and wherein preferably the C-terminus is amidated.

These peptides target the P-like subtypes of $Ca^{2+}$ channels as well as the N-type $Ca^{2+}$ channels. The ability to target P-like subtypes of $Ca^{2+}$ channels distinguishes these peptides from prior art ω-conotoxin peptides such as GVIA and MVIIA, which target only N-type $Ca^{2+}$ channels. Thus, the ω-conotoxin peptides of the present invention have utility common with prior ω-conotoxin peptides. One example is an immunoprecipitation assay with radiolabelled ω-conotoxin peptide which can be used to diagnose the Lambert-Eaton myasthenic syndrome, a disease in which autoimmune antibodies targeted to endogenous $Ca^{2+}$ channels are inappropriately elicited, thereby causing muscle weakness and autonomic dysfunction. In addition, the ω-conotoxin peptides of the present invention can be used for distinguishing types of $Ca^{2+}$ channels.

DESCRIPTION OF THE PREFERRED EMBODIMENT

Figure 1A:
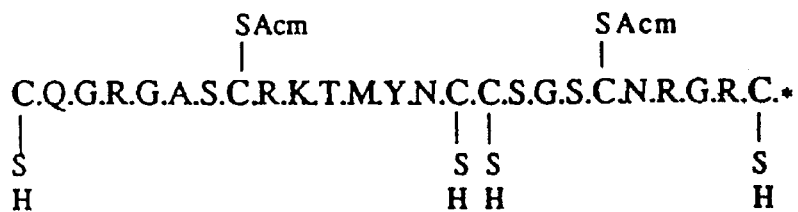
FIG. 1A shows the linear peptide amide of ω-conotoxin peptide MVIID following chemical synthesis.
Figure 1B:
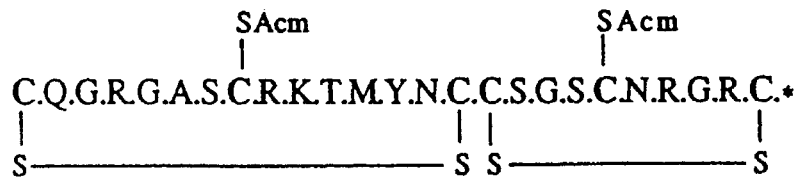
FIG. 1B shows one of the possible oxidation products of the peptide amide of FIG. 1A.
Figure 1C:
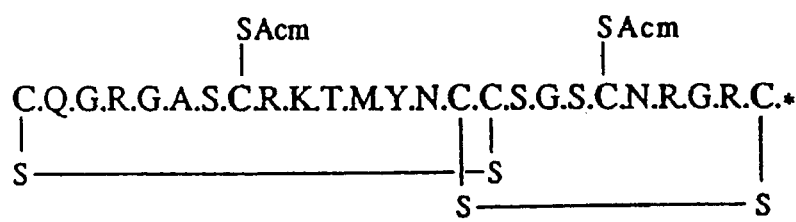
FIG. 1C shows one of the possible oxidation products of the peptide amide of FIG. 1A.
Figure 1D:
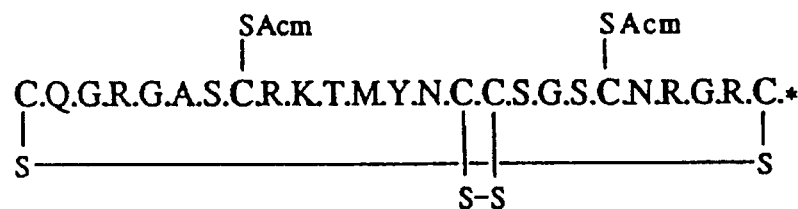
FIG. 1D shows one of the possible oxidation products of the peptide amide of FIG. 1A.
Figure 1E:
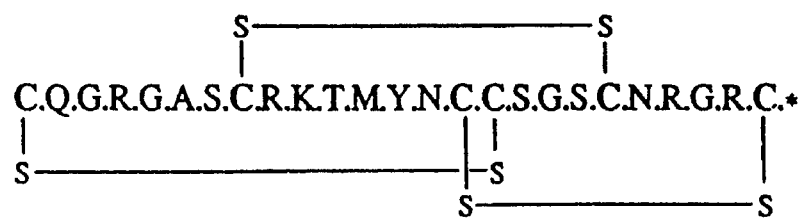
FIG. 1E shows the structure of ω-conotoxin peptide MVIID.

The present invention is directed to ω-conotoxin peptides having 24–30 amino acids, six cysteines which form disulfide bonds between the first and fourth, second and fifth, and third and sixth cysteines, respectively, and an internal sequence of Cys-Arg-Lys-Thr-Xaa$_1$-Tyr-Xaa$_2$-Cys-Cys-Ser-Gly-Ser-Cys (SEQ ID NO:1). While Xaa$_1$ can be any amino acid, it is preferred to be Met, Ser or Nle (norleucine).

Similarly, Xaa$_2$ can be any amino acid, but is preferred to be Asp or Asn. The invention is further directed to ω-conotoxin peptides of the generic formula Cys-Xaa$_1$-Gly-Xaa$_2$-Gly-Ala-Xaa$_3$-Cys-Arg-Lys-Thr-Xaa$_4$-Tyr-Xaa$_5$-Cys-Cys-Ser-Gly-Ser-Cys-Xaa$_6$-Arg-Gly-Xaa$_7$-Cys (SEQ ID NO:2). Preferably, the C-terminus is amidated. These peptides also contain three disulfide bonds, as described above. Each Xaa can be any amino acid. Preferably, each Xaa is as follows: Xaa$_1$ is Lys or Gln, Xaa$_2$ is Lys or Arg, Xaa$_3$ is Pro, Ser or Hyp (4-hydroxyproline), Xaa$_4$ is Asp or Asn, Xaa$_5$ is Gly-Arg or Asn and Xaa$_6$ is Lys or Arg.

Examples of ω-conotoxin peptides within the generic formula are MVIIC having the formula Cys-Lys-Gly-Lys-Gly-Ala-Xaa$_1$-Cys-Arg-Lys-Thr-Xaa$_2$-Tyr-Asp-Cys-Cys-Ser-Gly-Ser-Cys-Gly-Arg-Arg-Gly-Lys-Cys (SEQ ID NO:3), wherein Xaa$_1$ is preferably Pro or Hyp (4-hydroxyproline) and Xaa$_2$ is preferably Met or Nle (norleucine) and wherein preferably the C-terminus is amidated, and MVIID having the formula Cys-Gln-Gly-Arg-Gly-Ala-Ser-Cys-Arg-Lys-Thr-Xaa-Tyr-Asn-Cys-Cys-Ser-Gly-Ser-Cys-Asn-Arg-Gly-Arg-Cys (SEQ ID NO:4), wherein Xaa is preferably Met or Nle (norleucine), and wherein preferably the C-terminus is amidated. The disulfide bonds in each of these peptides are as described above.

These peptides appear to target the P-like subtypes of $Ca^{2+}$ channels as well as the N-type $Ca^{2+}$ channels. The ability to target P-like subtypes of $Ca^{2+}$ channels distinguishes these peptides from prior art ω-conotoxin peptides such as GVIA and MVIIA, which target only N-type $Ca^{2+}$ channels.

Any reagent that binds tightly to a specific cell surface site has value as a diagnostic reagent. ω-Conotoxin peptides MCIIC and MVIID appear to target a set of unique subtypes of calcium channels: these protein sites are not targeted by any other known reagent with such high affinity. The previously characterized ω-conotoxin peptides all have as their high affinity target a different calcium channel subtype (the N-type calcium channel). Thus, the peptides of the present invention have novel diagnostic use.

The use of calcium channel-targeted peptides in diagnostic work has already been methodically illustrated for ω-conotoxin peptide GVIA: a diagnostic test for the Lambert-Eaton syndrome has been developed based on the presence of ω-conotoxin peptide GVIA-sensitive sites on a neuroblastoma line. This work showed that calcium channel-specific reagents can be adapted to serve in more efficient diagnostic assays than were previously available. (The previous assay for Lambert-Eaton syndrome involved cumbersome electro-physiological procedures.) Since the ω-conotoxin peptides of the present invention also target GVIA-sensitive calcium channels, they also have utility for Lambert-Eaton syndrome. In addition, the ω-conotoxin peptides MVIIC and MVIID should reveal the presence or absence of calcium channels which are different from ω-conotoxin peptide GVIA-targeted calcium channels, and will thus add significantly to the diagnostic arsenal available for characterizing different cells expressing calcium channels of various types.

In addition to identifying different cell types, the peptides MVIIC and MVIID will serve as diagnostic reagents in pathology. The presence or absence of sites for the peptides can be determined in tissue sections. Because these peptides affect the control of respiratory rhythms in vivo, they can be used by pathologists as reagents to evaluate abnormalities in respiratory control. Pathologies of respiratory control are particularly severe in the neonatal period, and the use of these peptides as reagents for assessing neural developmental syndromes that result in respiratory crises is a further utility. The methodology for these utilities will parallel the methodology previously developed for ω-conotoxin peptide GVIA.

ω-Conotoxin peptides of the present invention are identified by molecular genetic techniques. Degenerative probes for ω-conotoxin peptides are prepared and used to screen cDNA libraries of Conus species. For example, degenerative probes for ω-conotoxin peptides isolated from *Conus magus* (MVIIA and MVIIB) are used to identify cDNA clones encoding ω-conotoxin peptide MVIIC. Additional cDNA clones are identified which cross-hybridize with a probe to MVIIC. In this manner, ω-conotoxin peptide MVIID is identified. ω-Conotoxin peptides from other Conus species are identified in a similar manner. Additionally, probes (degenerative or otherwise) to MVIIC, MVIID or the internal sequence described above are used to identify ω-conotoxin peptides from cDNA libraries of other Conus species. ω-Conotoxin peptides which are identified are synthesized or isolated as described further below. The resultant ω-conotoxin peptides are classified by their biological effect in fish, amphibians, mice and/or the like and by their receptor target specificities. The characterization of ω-conotoxin peptides which affect different ssubsets of $Ca^{2+}$ channels in mammalian brain is clearly desirable; every ω-conotoxin peptide exhibiting a new receptor target specificity provides an opportunity for functionally defining new subsets of channels. Recent molecular work strongly indicates that the number of different $Ca^{2+}$ channels in mammals is large (8–11). In addition, the electrophysiology of mammalian CNS neurons suggest that most will have multiple $Ca^{2+}$ channel subtypes in a single cell body. Therefore, there will be an urgent need for ligands which can discriminate functionally between closely related channel subtypes.

These peptides, which are generally termed ω-conotoxin peptides, are sufficiently small to be chemically synthesized. General chemical syntheses for preparing the foregoing ω-conotoxin peptides are described hereinafter, along with specific chemical syntheses of several ω-conotoxin peptides and indications of biological activities of these synthetic products. Various ones of these ω-conotoxin peptides can also be obtained by isolation and purification from specific Conus species using the technique described in U.S. Pat. No. 4,447,356 (12), the disclosure of which is incorporated herein by reference.

Although ω-conotoxin peptides can be obtained by purification from the enumerated cone snails, because the amounts of ω-conotoxin peptides obtainable from individual snails are very small, the desired substantially pure ω-conotoxin peptides are best practically obtained in commercially valuable amounts by chemical synthesis. For example, the yield from a single cone snail may be about 10 micrograms or less of ω-conotoxin peptide. By "substantially pure" is meant that the peptide is present in the substantial absence of other biological molecules of the same type; it is preferably present in an amount of at least about 85% by weight and preferably at least about 95% of such biological molecules of the same type which are present (i.e., water, buffers and innocuous small molecules may be present). Chemical synthesis of biologically active ω-conotoxin peptides depends of course upon correct determination of the amino acid sequence.

The ω-conotoxin peptides can also be produced by recombinant DNA techniques well known in the art. Such techniques are described by Sambrook et al. (13) The peptides produced in this manner are isolated, reduced if necessary, and oxidized to form the correct disulfide bonds.

One method of forming disulfide bonds in the ω-conotoxin peptides of the present invention is the air oxidation of the linear peptides for prolonged periods under cold room temperatures. This procedure results in the creation of a substantial amount of the bioactive, disulfide-linked peptides. The oxidized peptides are fractionated using reverse-phase high performance liquid chromatography (HPLC) or the like, to separate peptides having different linked configurations. Thereafter, either by comparing these fractions with the elution of the native material or by using a simple assay, the particular fraction having the correct linkage for maximum biological potency is easily determined. It is also found that the linear peptide, or the oxidized product having more than one fraction, can sometimes be used for in vivo administration because the cross-linking and/or rearrangement which occurs in vivo has been found to create the biologically potent conotoxin molecule. However, because of the dilution resulting from the presence of other fractions of less biopotency, a somewhat higher dosage may be required.

A second method of forming the disulfide bonds in the ω-conotoxin peptides of the present invention involves the use of acetamidomethyl (Acm) as protection agent on the second and fifth cysteines during the synthesis of the ω-conotoxin peptides. The use of Acm on these two residues is based on the analogy with disulfide bridges in other ω-conotoxin peptides. The peptide with the Acm protected cysteines is air-oxidized overnight at room temperature. The bicyclic peptides are separated by HPLC and the desired isomer isolated. The final disulfide bridge is carried out by iodination. The undesired isomers are efficiently recycled by reduction to linear peptide (1, FIG. 1). The desired isomer is determined by a partial reduction analysis (14). In this analysis, a sample of a bicyclic precursor is treated with tris-[2-carboxyethyl]-phosphine to give linear peptide (1, FIG. 1) and a singly-bridged intermediate. The latter peptide is reacted with iodoacetamide, and the location of alkylated cysteine residues is established by sequence analysis. In this analysis, it was determined that the correct linkages were between the first and fourth, second and fifth, and third and sixth cysteines.

The peptides are synthesized by a suitable method, such as by exclusively solid-phase techniques, by partial solid-phase techniques, by fragment condensation or by classical solution couplings. The employment of recently developed recombinant DNA techniques may be used to prepare these peptides, particularly the longer ones containing only natural amino acid residues which do not require post-translational processing steps.

In conventionl solution phase peptide synthesis, the peptide chain can be prepared by a series of coupling reactions in which the constituent amino acids are added to the growing peptide chain in the desired sequence. The use of various N-protecting groups, e.g., dicyclohexylcarbodiimide or carbonyldimidazole, various active esters, e.g., esters of N-hydroxyphthalimide or N-hydroxy-succinimide, and the various cleavage reagents, to carry out reaction in solution, with subsequent isolation and purification of intermediates, is well known classical peptide methodology. Classical solution synthesis is described in detail in the treatise, "Methoden der Organischen Chemie (Houben-Weyl): Synthese von Peptiden," (15). Techniques of exclusively solid-phase synthesis are set forth in the textbook, "Solid-Phase Peptide Synthesis," (16), and are exemplified by the disclosure of U.S. Pat. No. 4,105,603 (17). The fragment condensation method of synthesis is exemplified in U.S. Pat. No. 3,972,859 (18). Other available syntheses are exemplified by U.S. Pat. Nos. 3,842,067 (19) and 3,862,925 (20).

Common to such chemical syntheses is the protection of the labile side chain groups of the various amino acid moieties with suitable protecting groups which will prevent a chemical reaction from occurring at that site until the group is ultimately removed. Usually also common is the protection of an α-amino group on an amino acid or a fragment while that entity reacts at the carboxyl group, followed by the selective removal of the α-amino protecting group to allow subsequent reaction to take place at that location. Accordingly, it is common that, as a step in such a synthesis, an intermediate compound is produced which includes each of the amino acid residues located in its desired sequence in the peptide chain with appropriate side-chain protecting groups linked to various ones of the residues having labile side chains.

As far as the selection of a side chain amino protecting group is concerned, generally one is chosen which is not removed during deprotection of the α-amino groups during the synthesis. However, for some amino acids, e.g., His, protection is not generally necessary. In selecting a particular side chain protecting group to be used in the synthesis of the peptides, the following general rules are followed: (a) the protecting group preferably retains its protecting properties and is not split off under coupling conditions, (b) the protecting group should be stable under the reaction conditions selected for removing the α-amino protecting group at each step of the synthesis, and (c) the side chin protecting group must be removable, upon the completion of the synthesis containing the desired amino acid sequence, under reaction conditions that will not undesirably alter the peptide chain.

It should be possible to prepare many, or even all, of these peptides using recombinant DNA technology. However, when peptides are not so prepared, they are preferably prepared using the Merrifield solid-phase synthesis, although other equivalent chemical syntheses known in the art can also be used as previously mentioned. Solid-phase synthesis is commenced from the C-terminus of the peptide by coupling a protected α-amino acid to a suitable resin. Such a starting material can be prepared by attaching an α-amino-protected amino acid by an ester linkage to a chloromethylated resin or a hydroxymethyl resin, or by an amide bond to a benzhydrylamine (BHA) resin or paramethylbenzhydrylamine (MBHA) resin. Preparation of the hydroxymethyl resin is described by Bodansky et al. (21). Chloro-methylated resins are commercially available from Bio Rad Laboratories (Richmond, Calif.) and from Lab. Systems, Inc. The preparation of such a resin is described by Stewart et al. (16). BHA and MBHA resin supports are commercially available, and are generally used when the desired polypeptide being synthesized has an unsubstituted amide at the C-terminus. Thus, solid resin supports may be any of those known in the art, such as one having the formulae —O—$CH_2$-resin support, —NH BHA resin support, or —NH-MBHA resin support. When the unsubstituted amide is desired, use of a BHA or MBHA resin is preferred, because cleavage directly gives the amide. In case the N-methyl amide is desired, it can be generated from an N-methyl BHA resin. Should other substituted amides be desired, the teaching of U.S. Pat. No. 4,569,967 (22) can be used, or should still other groups than the free acid be desired at the C-terminus, it may be preferable to synthesize the peptide using classical methods as set forth in the Houben-Weyl text (15).

The C-terminal amino acid, protected by Boc and by a side-chain protecting group, if appropriate, can be first coupled to a chloromethylated resin according to the procedure set forth in K. Horiki et al. (23), using KF in DMF at about 60° C. for 24 hours with stirring, when a peptide having free acid at the C-terminus is to be synthesized. Following the coupling of the BOC-protected amino acid to the resin support, the α-amino protecting group is removed, as by using trifluoroacetic acid (TFA) in methylene chloride or TFA alone. The deprotection is carried out at a temperature between about 0° C. and room temperature. Other standard cleaving reagents, such as HCl in dioxane, and conditions for removal of specific α-amino protecting groups may be used as described in Schroder & Lubke (24).

After removal of the α-amino-protecting group, the remaining α-amino- and side chain-protected amino acids are coupled step-wise in the desired order to obtain the intermediate compound defined hereinbefore, or as an alternative to adding each amino acid separately in the synthesis, some of them may be coupled to one another prior to addition to the solid phase reactor. Selection of an appropriate coupling reagent is within the skill of the art. Particularly suitable as a coupling reagent is N,N'-dicyclohexylcarbodiimide (DCC).

The activating reagents used in the solid phase synthesis of the peptides are well known in the peptide art. Examples of suitable activating reagents are carbodiimides, such as N,N'-diisopropylcarbodiimide and N-ethyl-N'-(3-dimethylaminopropyl)carbodiimide. Other activating reagents and their use in peptide coupling are described by Schroder & Lubke (24) and Kapoor (25).

Each protected amino acid or amino acid sequence is introduced into the solid-phase reactor in about a twofold or more excess, and the coupling may be carried out in a medium of dimethylformamide (DMF): $CH_2Cl_2$ (1:1) or in DMF or $CH_2Cl_2$ alone. In cases where intermediate coupling occurs, the coupling procedure is repeated before removal of the α-amino protecting group prior to the coupling of the next amino acid. The success of the coupling reaction at each stage of the synthesis, if performed manually, is preferably monitored by the ninhydrin reaction, as described by Kaiser et al. (26). Coupling reactions can be performed automatically, as on a Beckman 990 automatic synthesizer, using a program such as that reported in Rivier et al. (27).

After the desired amino acid sequence has been completed, the intermediate peptide can be removed from the resin support by treatment with a reagent, such as liquid hydrogen fluoride, which not only cleaves the peptide from the resin but also cleaves all remaining side chain protecting groups and also the α-amino protecting group at the N-terminus if it was not previously removed to obtain the peptide in the form of the free acid. If Met is present in the sequence, the Boc protecting group is preferably first removed using trifluoroacetic acid (TFA)/ethanedithiol prior to cleaving the peptide from the resin with HF to eliminate potential S-alkylation. When using hydrogen fluoride for cleaving, one or more scavengers such as anisole, cresol, dimethyl sulfide and methylethyl sulfide are included in the reaction vessel.

Cyclization of the linear peptide is preferably affected, as opposed to cyclizing the peptide while a part of the peptidoresin, to create bonds between Cys residues. To effect such a disulfide cyclizing linkage, fully protected peptide can be cleaved from a hydroxy-methylated resin or a chloromethylated resin support by ammonolysis, as is well known in the art, to yield the fully protected amide intermediate, which is thereafter suitably cyclized and deprotected. Alternatively, deprotection, as well as cleavage of the peptide from the above resins or a benzhydrylamine (BHA)

resin or a methylbenzhydrylamine (MBHA), can take place at 0° C. with hydrofluoric acid (HF), followed by oxidation as described above.

ω-Conotoxin peptides MVIIC and MVIID are illustrative species of the generic invention. The synthetic ω-conotoxin peptide MVIIC has the expected biological activity; it paralyzes fish, displaces specific binding of $^{125}$I-ω-conotoxin peptide GVIA to membrane binding sites, and inhibits $^{45}Ca_{2+}$ entry into synaptosomes. In many vertebrate systems, ω-conotoxin peptides MVIIC and GVIA have closely overlapping specificity and cause the same symptomatology upon injection. However, in mammalian systems, the two peptides have strikingly different in vivo biological activity. In contrast to the characteristic shaker syndrome elicited by ω-conotoxin peptide GVIA, ω-conotoxin peptide MVIIC causes mice to gasp for breath and is lethal. These striking differences in in vivo symptoms are already indicative that, in the mammalian central nervous system, the two peptides interact with different subsets of $Ca^{2+}$ channels.

The electrophysiological studies directly demonstrate that ω-conotoxin peptide GVIA is more narrowly targeted with respect to $Ca^{2+}$ channel subtypes than is ω-conotoxin peptide MVIIC, and that in the mammalian CNS, GVIA targets may be a subset of MVIIC-sensitive $Ca^{2+}$ channels. Both the electrophysiological data and the synaptosome data clearly demonstrate that MVIIC inhibits $Ca^{2+}$ channels that are GVIA-resistant. The binding experiments provide direct binding evidence for the broader specificity of MVIIC under physiological conditions; MVIIC is able to completely displace the high affinity GVIA binding, but GVIA and MVIIA are unable to displace the high affinity MVIIC binding.

The effects of ω-conotoxin peptide MVIIC on neurotransmitter release have been directly tested in a few systems, and it has been found that MVIIC will inhibit the GVIA-resistant depolarization-induced release of norepinephrine and γ-aminobutyric acid. These results, and the MVIIC sensitivity of $^{45}Ca^{2+}$ uptake by synaptosomes, strongly suggest that a significant fraction of synaptic $Ca^{2+}$ channels which control neurotransmitter release are in the MVIIC-sensitive, GVIA-resistant class. However, a class of cell body $Ca^{2+}$ channels, often referred to as "P" channels (because they were originally described in cerebellar Purkinje cells (28)) are also MVIIC-sensitive and GVIA-resistant. It will be of considerable interest to determine how heterogeneous the MVIIC-sensitive, GVIA-sensitive mammalian $Ca^{2+}$ channel subclass is—will there be a coherent group of "P-like" $Ca^{2+}$ channels that differ only slightly from each other, or will there be channel targets that belong to considerably divergent channel subtypes? It is clearly relevant in this regard to compare both structure and activity of ω-agatoxin IVA, the polypeptide toxin from spider venom which blocks "P" channels (29). ω-Agatoxin IVA is a 48 amino acid peptide with four disulfide bonds, with no obvious homology in sequence to ω-conotoxin peptide MVIIC. Furthermore, the data presented below in Table 3 demonstrate that ω-agatoxin IVA does not block $^{125}$I-ω-conotoxin peptide MVIIC binding to its high affinity sites. This result suggests that the high affinity ω-conotoxin peptide MVIIC sites are either on a different $Ca^{2+}$ channel subtype altogether from the ω-agatoxin IVA binding sites, or that the two toxins act at different sites on the same $Ca^{2+}$ channel complex.

It has been found that ω-conotoxin peptide MVIID exhibits a marked preference for "non-N type" vs. N-type mammalian $Ca^{2+}$ channels. The in vivo effects of the peptide upon IC injection in mice are strikingly different from N-channel targeted ω-conotoxin peptide GVIA and more closely resemble that of ω-conotoxin peptide MVIIC. Furthermore, unlike GVIA, the new peptide inhibits synaptosomal voltage-sensitive $^{45}Ca^{2+}$ uptake. Finally, MVIID has a much higher affinity for the MVIIC site than for the GVIA binding site; indeed, under the conditions used, it shows a greater discrimination between these two binding sites than any other ω-conotoxin. Thus, ω-conotoxin peptide MVIID is a ligand for voltage-gated $Ca^{2+}$ channels other than the N-subtype.

The data strongly indicates that the peptide has effects on P-like subtypes of $Ca^{2+}$ channels. The P-type channel was originally characterized from cerebellar Purkinje cells (28). This $Ca^{2+}$ current was sensitive to the spider toxin ω-agatoxin IVA (29) but insensitive to ω-conotoxin peptide GVIA and dihydropyridines, a pharmacological profile also exhibited by $^{45}Ca^{2+}$ uptake by synaptosomes in vitro (hence the term "P-like"). In addition, because ω-conotoxin peptide MVIID displaces ω-conotoxin peptide MVIIC, it appears to have high affinity for the non-N, non-L type high affinity MVIIC site, which appears to be distinct from the P-type $Ca^{2+}$ channel. Thus, the peptide appears to target additional voltage-gated $Ca^{2+}$ channel subtypes in the mammalian CNS.

Four calcium channel antagonists from spider and cone snail venoms (ω-agatoxin IVA and ω-agatoxin IIIA from *Agelenopsis aperta* and ω-conotoxin peptides GVIA and MVIIC are radioiodinated and used as probes to characterize their $Ca^{2+}$ channel target sites in rat brain membranes. All radiolabelled toxin derivatives showed specific, high affinity binding to rat brain receptors; $IC_{50}$ values were 30 nM for [$^{125}$I]ω-agatoxin IVA and 0.5 nM for [$^{125}$I]ω-agatoxin IIIA. Binding sites for the two ω-agatoxin peptides appeared to be completely non-overlapping. In addition, unlabelled ω-agatoxin IIIA competed for binding to high affinity sites defined by the radiolabelled conotoxin peptides, whereas ω-agatoxin IVA did not.

These results suggest that there are two distinct ligand sites on P-type channels, one specific for ω-agatoxin IVA and the other targeted by ω-agatoxin IIIA and ω-conotoxin peptide MVIIC. ω-Agatoxin IVA is a selective blocker of P-type calcium channels; the high affinity binding sites for this ligand are consistent with specific binding to this subtype of calcium channels. ω-Agatoxin IIIA does not compete with [$^{125}$I]ω-agatoxin IVA for binding to its high affinity sites. Using synaptosomal and $^{45}Ca_{2+}$ uptake to assay P-type calcium channels, ω-agatoxin IIIA was found to functionally occlude the effects of ω-conotoxin peptide MVIIC, but not those of ω-agatoxin IVA. These data, and other electrophysiological results, indicate that ω-agatoxin IIIA and ω-conotoxin peptide MVIIC bind to the same general site on P-type channels, distinct from the ω-agatoxin IVA site. However, the two ligand sites apparently interact with each other, since occupancy of the ω-conotoxin peptide MVIIC site causes a decreased affinity of ω-agatoxin IVA for its binding site. The high affinity [$^{125}$I]ω-conotoxin peptide binding site is distinct from the P-type channel; under the binding conditions used, unlabelled MVIIC displaces [$^{125}$I] MVIIC with subnanomolar affinity, but micromolar concentrations are required to displace [$^{125}$I]ω-agatoxin IVA. This novel high affinity is termed herein an O-type site, which may correspond to a calcium channel subtype similar to, but pharmacologically distinct from P- and N-type calcium channels. Neither ω-agatoxin IVA nor ω-conotoxin peptide GVIA can displace MVIIC binding to the O-type site, although ω-agatoxin IIIA prevents MVIIC binding.

Thus, four calcium channel ligands, the dihydropyridines, ω-conotoxin peptide GVIA, ω-agatoxin IVA and ω-conotoxin peptide MVIIC, define four high affinity binding sites which appear to be present on different calcium channel subtypes, the L-, N-, P- and O-type calcium channels, respectively. The use of radiolabelled high affinity ligands from spider and cone snail venoms provides a framework for a biochemical classification of calcium channel subtypes that is consistent with electrophysiological data.

EXAMPLES

The present invention is described by reference to the following Examples, which are offered by way of illustration and are not intended to limit the invention in any manner. Standard techniques well known in the art or the techniques specifically described below were utilized.

Example 1

Identification of ω-Conotoxin Peptide MVIIC Sequence

Screening of cDNA Libraries cDNA clones encoding the ω-conotoxin peptide MVIIC were isolated from a size-fractionated cDNA library constructed from C. magus venom duct mRNA. The cDNA library was size-fractionated into insets with average size of 74 Kb, 2 Kb, 1 Kb and 0.5 Kb. The two smallest size fractions were screened. Clones were initially identified by screening with probes designed to identify DNA sequences encoding the related C. magus ω-conotoxin peptides MVIIA and MVIIB (7). Oligonucleotides were synthesized on an Applied Biosystems 380B synthesizer. Approximately 16 pmols of a mixed oligonucleotide 17 mer, DHOG101 (5'-GTRCARCARTCRTACAT-3', where R=A or G; SEQ ID NO:5) corresponding to the MVIIA and MVIIB amino acid sequence MYDCCT (SEQ ID NO:6) were end-labelled with [γ-$^{32}$P]ATP using T4 polynucleotide kinase (13) and hybridized to two of four replica nitrocellulose filters for 50 hrs at 50° C. in 3M TMAC (Aldrich Chemical Company, Milwaukee, Wis.), 50 mM Tris (pH 8.0) and 0.2% SDS. Following sequential washing at room temperature in 2× SSC and 0.1% SDS, positive colonies were identified by autoradiography. From this initial pool of clones, MVIIB-encoding clones were eliminated by subtractive hybridization. Duplicate replica filters were hybridized as described above with a $^{32}$P end-labelled oligonucleotide (DHOG-57) containing the unique sequence 5'-GAAGTCCTATGACATGA-3' (SEQ ID NO:7) from an authentic MVIIB cDNA clone. Colonies which hybridized to the general probe, but failed to hybridize with the specific probe, were prepared for DNA sequencing.

Sequencing

Five μg of DNA were denatured in 0.4M NaOH at 37° C. for 30 min. The solution was then neutralized by adding ammonium acetate to a final concentration of 0.4M, and the DNA precipitated with two volumes of absolute ethanol. The DNA was pelleted, resuspended in 8 μl of H$_2$O, and annealed with 2 pmols of primer by heating to 65° C. for 5 min and cooling slowly to 30° C. The DNA was sequenced using the Sequenase Version 2.0 DNA sequencing kit. Labelling and termination reactions were carried out according to protocol in the Sequenase Version 2.0 4th Edition Manual (United States Biochemical, 1990). The nucleic acid sequence and presumptive translation product for this cDNA clone are shown as SEQ ID NO:8 and SEQ ID NO:9, respectively. It is expected that the C-terminal glycine residue, characteristic of many conotoxin precursors, would be post-translationally processed into an amide; thus, the peptide is predicted to be blocked at the C-terminus. The predicted mature peptide, beginning with the first cysteine residue, has been designated ω-conotoxin peptide MVIIC.

Example 2

Identification of ω-Conotoxin Peptide MVIID Sequence

Screening of cDNA Libraries

ω-Conotoxin MVIID-encoding clones were identified with the subtraction screening strategy described in Example 1. The clones of interest hybridized to DHOG101 but not to DHOG257. Sixty-seven clones hybridized to the generic probe with 53 of these hybridizing to the MVIIB-specific probe. Three clones also cross-hybridized with the probe designed to recognize cDNA clones encoding a related toxin, MVIIC, as described in Hillyard et al. (30). Approximately 16 pmol of a 17-mer oligonucleotide probe, DHOG280 (5'-CCATGTCGTAAGACTAT-3') (SEQ ID NO:10) encoding the MVIIC toxin region PCRKTM (SEQ ID NO:11), was 5'-end labelled with [γ-$^{32}$P]ATP using T4 polynucleotide kinase (13) and hybridized to two of six prehybridized replica nitrocellulose filters for 50 hrs at 50° C. in 3M tetramethylammonium chloride (Aldrich Chemical Company, Milwaukee, Wis.), 0.5M sodium phosphate, 1 mM EDTA, 5× Denhardt's solution, 100 μg/ml of sheared salmon DNA and 0.6% SDS. After sequential washing of filters at room temperature to a final stringency of 2× SSC and 0.1% SDS, positive colonies were identified by autoradiography. Clones were sequenced in both strands.

Sequencing of DNA

All sequencing reactions were performed using the dideoxy chain termination technique with Sequenase 2.0 DNA Sequencing Kit (United States Biochemical, 1990). Two pUC13 targeting primers and three customized internal oligonucleotide primers were used for sequencing the two strands of the cDNA insert. Oligonucleotides were synthesized using an Applied Biosystems 380B synthesizer.

5 μg of the CsCl-purified plasmid DNA sample in TE were dentured in 0.4M NaOH at room temperature for 5 min. The solution was then neutralized with NH$_4$OAc to a final concentration of 0.4M, and 2 volumes of absolute alcohol were added to precipitate the DNA at −70° C. The DNA pellet was washed with 80% EtOH and air-dried. The primer (11 ng) was added and annealed by heating the tube to 65° C. for 5 min and cooling slowly to 30° C. over a period of about 20 min. The labelling, extension and termination reactions were performed following protocol in the Sequenase Version 2.0 Manual, 4th Edition, 1990 (United States Biochemical). Two of the three clones sequenced encoded ω-conotoxin peptide MVIIC. The nucleic acid sequence and presumptive translation product for the third cDNA clone are shown as SEQ ID NO:12 and SEQ ID NO:13, respectively. It is expected that the C-terminal glycine residue would be post-translationally processed into an amide; thus, the peptide is predicted to be blocked at the C-terminus. The predicted mature peptide, beginning with the first cysteine residue, has been designated ω-conotoxin peptide MVIID.

Example 3

Synthesis of ω-Conotoxin Peptide MVIIC

In order to further characterize ω-conotoxin peptide MVIIC, the predicted mature peptide was synthesized from its amino acid sequence (SEQ ID NO:3). Since it was assumed that the disulfide bonding was similar to MVIIA and MVIIB, the conditions used for oxidizing cysteine residues to form disulfide bonds were those previously developed for other ω-conotoxin peptides (31). Because it was uncertain whether the proline residue in position 7 is hydroxylated (many proline residues in conotoxins are hydroxylated), both the 4-hydroxyproline and prolyl forms of the peptide were synthesized. Since the presence of a methionine residue interferes with radio-labelling, a peptide in which norleucine replaced methionine in position 12 was synthesized. No detectable differences in activity were found between the prolyl and the hydroxyprolyl forms of the peptide and between the norleucyl and methionyl forms of the peptide. In all of the studies below, the peptide with proline and methionine was used. An amino acid sequencing run carried out on both synthetic peptides confirmed the sequence.

The peptide was synthesized on a replumbed ABI model 430A peptide synthesizer, using standard t-butyloxycarbonyl (tBOC) chemistry with some modifications (4). The synthesis was started from 0.4 mmole MBHA resin (0.61–0.66 m $NH_2$ per g; Advanced Chem. Tech.), single-coupling the first nine amino acids (except Arg and Asn, which are always double-coupled as active esters formed from 1-hydroxybenzotriazole (HOBt) with DCC), and double-coupling the remainders (the first couplings were in DCM, the second couplings in DMFA solution). Amino acid side chain protections were Arg(Tos), Asp(OBzl), Cys(4-MeBzl), Hyp(Bzl), Lys(CIZ), Ser(Bzl), Thr(Bzl), Tyr(BrZ). In order to obtain 95+% overall efficiency of synthesis, the coupling steps were monitored with the ninhydrin test and were repeated to achieve 99.5+% amino acid incorporation yield in each cycle.

The peptide was cleaved from the resin (1 g) in liquid HF (15 ml, −10° to 0° C.) containing 10% p-Cresol. The cleavage time varied between 80–95 min. The HF was removed with a strong stream of nitrogen, the oily residue was washed with cold AcOEt (three times with 20 ml, −30° C.) filtered and the peptide was extracted by washing the residue with 15 ml water, three times with 15 ml 50% AcOH, and once with 15 ml water. The combined aqueous extracts were lyophilized.

Typically, 300 mg of crude lyophilized product was dissolved in 24 ml solution of guanidine hydrochloride (3M), NH4OAc (0.32M) and DTT (≈10 equivalents of the pepide). The mixture was stirred for 1 to 1.5 hr at ambient temperature, then diluted with 120 ml water and stirred while exposed to the atmosphere at +4° C. The progress of the oxidation was monitored with HPLC and completion was confirmed with the Ellman test (at the end, the free SH content was usually less than 5% of the starting value). Upon completion of the disulfide formation, the solution was acidified to pH ≈3.5 with acetic acid, concentrated under vacuum to approximately 15–20 ml, and gel-filtered on a Sephadex G-25 column (2.5×60 cm) euting with 0.5M AcOH. Pooled prepurified peptide fractions were further purified on a preparative HPLC column (Rainin Dynamax system, 4.14×30 cm, C-18 reversed phase packing material, 300 Å pore size, 12 μm particle size) using 0.1% TFA in water/0.1% TFA in acetonitrile gradient elution solvent system (40 ml/min pumping rate). The pure fractions were pooled and lyophilized. Yield of purified peptide was usually 10%–16%, based on the loading capacity of the MBHA-resin.

The synthetic peptides were analyzed for their disulfide bonding conformation. Results confirmed that ω-conotoxin peptide MVIIC has the same disulfide bonding conformation as other ω-conotoxins, i.e., three disulfide linkages at $Cys^1$-$Cys^{16}$, $Cys^8$-$Cys^{20}$ and $Cys^{15}$-$Cys^{26}$.

Example 4

Synthesis of ω-Conotoxin Peptide MVIID

Chemical synthesis was based on the predicted amino acid sequence (SEQ ID NO:4) and disulfide bridges were placed by analogy with other ω-conotoxin peptides. Efficient closure of the bridges was achieved by focusing the synthesis into a preferred path. Stable acetamidomethyl protection (32) was placed on $Cys^8$ and $Cys^{20}$, designed to become one desired bridge. The other four cysteines were protected during synthesis by acid-labile trityl groups, which were removed concomitantly with release of peptide from the resin by TFA. Since the presence of a methionine residue interferes with radiolabelling, a peptide in which norleucine replaced methionine in position 12 was synthesized. No detectable differences in activity were found between the norleucyl and methionyl forms of the peptide. In all studies below, the methionyl form was used.

The peptide chain was built on Rink amide resin by Fmoc procedures with HBTU couping, using an ABI Model 430 peptide synthesizer. Most amino acid derivatives were purchased from Bachem (Torrance, Calif.), and loaded into cartridges: exceptions were Fmoc-Arg(pmc), Fmoc-Gln (trt) and Fmoc-Asn (trt), which were purchased from ABI (Foster City, Calif.). Side-chain protection of non-Cys residues was in the form of t-butyl (Ser, Thr, Tyr), Boc (Lys), Pmc (Arg), Trt (Asn, Gln). Orthogonal protection was used on cysteines: Trt on residues 1, 15, 16 and 25, and Acm (32) on residues 8 and 20. After assembly of the resin-bound peptide, the terminal Fmoc group was removed in situ by treatment with 20% piperidine in DMF.

Linear peptide amide 1 (see FIG. 1) was released from the resin by treatment with a mixture of TFA: $H_2O$: thioanisole: dithioethane: phenol (10: 0.5: 0.5: 0.25: 0.75 by volume). Because of the presence of several Arg(pmc) residues, cleavage was extended to 2.5 hours at 20° C. Released peptide was precipitated by filtering the reaction mixture into methyl-t-butyl ether (MTBE) which had been chilled to −10° C. The precipitate was washed a further three times with MTBE, and the supernatants were discarded. Pelleted peptide was dissolved by addition of 0.1% TFA in 60% acetonitrile, with gentle swirling. The linear peptide amide was purified by reversed phase HPLC using a gradient of acetonitrile in 0.1% TFA on a Vydec C18 column.

Peptide 1, containing four unprotected Cys residues, was then oxidized to a mixture of three bicyclic isomers (2–4) (see FIG. 1), by adjusting the solution to pH 7.0 with solid Tris, and allowing the mixture to stir at room temperature overnight. The three isomers were separated by HPLC. Closure of the third bridge ($Cys^8$–$Cys^{20}$) was carried out by iodine oxidation on samples of two of the three isomers. For this, approximately 10 nmol of bicyclic peptide was dissolved in 10 μl of TFA and mixed with 100 μl of iodine solution (20 mM in 80% acetic acid). Reaction was allowed to proceed for 15 min in the dark at 20° C. and was terminated by addition of 100 μl of 0.3M ascorbic acid (33). The solution was then diluted with water to reduce acetic acid concentration below 5%, and injected directly into the HPLC column for purification of the tricyclic peptides.

The peptide has also been synthesized by the standard procedure used for ω-conotoxin peptides MVIIC and SVIB (30, 34).

Disulfide Bridge Analysis

Direct placement of one bridge was assured by using the Acm protecting group for $Cys^8$ and $Cys^{20}$, by analogy with other ω-conotoxin peptides. To establish connectivities of the other two bridges in the biologically active isomer, a sample of its bicyclic precursor was analyzed by partial reduction (14). Treatment with 10mM tris-[2-carboxyethyl]-phosphine (35) for five minutes at pH 3.0 gave a mixture of 1 (FIG. 1) and a singly-bridged intermediate. The latter peptide was reacted with iodoacetamide, and location of alkylated cysteine residues was established by sequence analysis. The singly-bridged reduction intermediate was found to be labelled by Acm on $Cys^8$ and $Cys^{20}$ and by iodoacetamided The analysis also confirmed the correctness of the sequence as built.

Example 5

Assay Methods

A. Electrophysiological Methods

Pyramidal neurons were dissociated from the CA1 region of the hippocampus and Purkinje neurons from the cerebellar vermis of 7- to 21-day-old Long-Evans rats. Slices were incubated at 37° C. for 8–10 min in a solution containing 3 mg/ml protease XXIII (Sigma, St. Louis, Mo.), 82 mM $Na_2SO_4$, 30 mM $K_2SO_4$, 5 mM $MgCl_2$, 2 mM HEPES, 10 mM glucose and 0.001% phenyl red indicator, pH 7.4. Slices were then stored in a solution containing 1 mg/ml bovine serum albumin (BSA) (Sigma, St. Louis, Mo.), 1 mg/ml trypsin inhibitor (Sigma), 82 mM $Na_2SO_4$, 30 mM $K_2SO_4$, 5 mM $MgCl_2$, 10 mM HEPES, 20 mM glucose and 0.001% phenyl red indicator, pH 7.4, and triturated to release cells. Whole-cell $Ca^{2+}$ channel currents (36) were recorded with 1.5–7 ω pipettes made from Boralex glass (Dynalab, Rochester, N.Y.) containing an internal solution of 108 mM cesium-methanesulfonate, 4 mM $MgCl_2$, 9 mM EGTA, 9 mM HEPES, 4 mM Mg-ATP, 14 mM creatine phosphate (Tris salt), 1 mM GTP (Tris salt), pH 7.4. The external solution for recording $Ca^{2+}$ channel currents was 5 mM $BaCl_2$, 160 mM TEA-Cl, 0.1 mM EGTA, 10 mM HEPES, pH 7.4.

B. Measurement of $^{45}Ca^{2+}$ Uptake in Synaptosomes

The procedures used are slightly modified from those previously described (31). Three freshly obtained rat brains (adult, Sprague-Dawley) were homogenized in 30 ml of 0.32M sucrose, 20 mM Na-HEPES, pH 7.4, in a glass/Teflon homogenizer (Wheaton) using 10 up-and-down strokes at 700 rpm. The homogenate was centrifuged at 3,600 rpm for 10 minutes in a Sorvall SS-34 rotor, and the resulting pellet discarded. The supernatant was respun at 12,500 rpm for 20 minutes in the above rotor. The supernatant was discarded and the pellet resuspended in 3 ml/brain "$Ca^{2+}$ free $Na^+$+ 5K" (5 mM KCl, 1.4 mM $MgCl_2$, 1.2 mM $NaH_2PO_4$, 10 mM glucose, 145 mMNaCl, 20 mM HEPES, with Tris used to adjust pH to 7.4 at room temperature). 20 ml of this synaptosome mixture was then transferred to each reaction tube. 25 ml of "$Ca^{2+}$ free Na+5K" was added to each tube, followed by 5 µl of toxin dissolved in a 0.5% lysozyme solution, or 5 µl of lysozyme solution alone. The reaction mix was then incubated for 30 min at room temperature. Uptake was initiated by 50 ml of either "low $K^+$" (which has the same components as $Na^+$+5K, plus the addition of 1 mM $CaCl_2$ and 20 µCi/ml $^{45}Ca^{2+}$) or 50 ml of "high $K^+$" (same as "low $K^+$" except that KCl is 137 mM instead of 5 mM and NaCl is omitted). Thus, the final reaction mix is 100 µl, and "high $K^+$" reaction tubes are thus depolarized with 71 mM $K^+$. Toxin concentrations were calculated based on this final volume. Uptake was terminated approximately 1–2 seconds later by the addition of 30 mM EGTA in 120 mM NaCl, 5 mM KCl (adjusted with Tris base to pH 7.6 at room temperature), and then by rapidly filtering using a Skatron cell harvester (Lier, Norway) with Skatron #11734 filtermats. Wash was performed for 24 seconds (flow is approximately 0.5 ml/min) with a subsequent 10 second drying time. Wash medium contained 5 mM KCl, 1.4 mM $MgCl_2$, 1 mM $CaCl_2$, 145 mM NaCl, 20 mM HEPES adjusted with Tris to pH 7.4 at room temperature. Wash medium was used at room temperature. Filters were then dried, and 4 ml of Beckman Ready Safe scintillation fluid was added. Samples were then counted for one minute with counting repeated three times. Each data point was done in duplicate, and the values averaged. 100% uptake was defined as the difference between "high $K^+$" and "low $K^+$." Toxin data points were then defined as percentage of this value.

The uptake of $^{45}Ca^{2+}$ into rat brain synaptosomes was carried out as described in Example 5B for MVIID except that all solutions with low $K^+$ contained 140 mM NaCl (instead of 145 mM), and the high $K^+$-containing solution contained 8 mM NaCl (instead of none).

C. Behavioral Assays

The biological activity of a MVIID was assayed using intracranial (IC) injections of peptide in mice as previously described (1). ω-conotoxin peptide MVIID was dissolved in normal saline and injected IC into 3–4 week-old mice weighing from 5–11 g.

D. Iodination of MVIIC

The conotoxin peptide was iodinated by the method of Cruz and Olivera (2) using [$^{125}$I]NaI (2.0 mCi/nmole) as label and Iodogen as the solid-phase reagent. After iodination, the reaction mix was extracted two times with 700 µl of ethyl acetate, then the aqueous phase dried in vacuo. The residue was dissolved in 100 µl of 0.1% TFA and purified by HPLC using an analytical Vydec $C_{18}$ column eluted with a gradient of acetonitrile in 0.1% TFA a a flow rate of 1 ml/min. Two major peaks of iodinated derivatives were obtained and the later eluting iodinated peak was used.

E. Rat Cortex Membrane preparation

Crude membranes were prepared from adult rat cortices. Thirty grams of frozen adult rat cerebellar cortices were ground to a fine powder in liquid nitrogen with a mortar and pestle. Subsequent procedures were performed at 0°–4° C. The powdered tissue was hand-homogenized using a glass/Teflon homogenizer in 200 ml of lysis buffer containing 20 mM HEPES (pH 7.4), 10 mM sodium pyrophosphate, 1 mM EGTA, 1 mM EDTA, 1 mM sodium orthovanadate, 2 µM leupeptin, 1 µM pepstatin, 1 mM o-phenanthroline and 1 mM PMSF. Homogenization consisted of two strokes of the pestle every 15 min for one hour. The homogenate was spun at 2,800×g for 2 min and the supernatant was collected and spun at 100,000×g for 20 min. The resulting pellet was resuspended and washed three times (100,000×g for 20 min) in 0.32M sucrose, 20 mM HEPES/Tris (pH 7.4), 2 µM leupeptin, 1 µM pepstatin, 1 mM o-phenanthroline and 1 mM PMSF (SHT with protease inhibitors). The resulting pellet was resuspended in a minimal volume of SHT with protease inhibitors, and aliquots were frozen in liquid nitrogen for storage at −70° C.

F. Filter Binding Assay

The binding of $^{125}$I-labelled MVIIC to crude rat membrane preparations was measured using 100 µl of assay mix which contained the following: 7.2–14.4/µg of membrane protein, carrier-free $^{125}$I-ω-conotoxin peptide MVIIC (80–230 kcpm), 0.02 mg/ml lysozyme, 0.32M sucrose and 5 mM HEPES/Tris (pH 7.4). Assays were done with or without 0.02% sodium cholate. Non-specific binding was measured by preincubating the membrane preparation with 0.5 µM unlabelled MVIIC for 30 min on ice before $^{125}$I-ω-conotoxin peptide MVIIC was added. The amount of binding inhibited by the presence of the unlabelled peptides was similarly measured by preincubating with each specific amount of the cold ligand. The final assay mix was then incubated at room temperature for 30–40 min and diluted with 3 ml of ice-cold medium containing 160 mM choline chloride, 5 mM HEPES/Tris (pH 7.4), 1.5 mM CaCl$_2$, 1 mg/ml bovine serum albumin and 0.05% Tween 20. Membranes were collected on glass fiber filters (Whatman GF/C or Skatron 11734 soaked in 0.1% polyethylenimine) under vacuum and washed three times with 3 ml of wash medium. The amount of radioactivity on the filters was measured.

Filter binding assays (2) were used to measure the binding of $^{125}$I-ω-conotoxin peptide MVIIC and $^{125}$I-ω-conotoxin peptide GVIA to crude rat cortex membrane preparations. The assay mix (200 ||l) contained the following: 30 µg of membrane protein, carrier-free $^{125}$I-ω-conotoxin peptide MVIIC or $^{125}$I-ω-conotoxin peptide GVIA (40–160 Kcpm), 0.2 mg/ml lysozyme, 0.32M sucrose, 20 mM HEPES/Tris (pH 7.4). Non-specific binding was measured by preincubating the membrane preparation with 0.5–1.0 µM unlabelled MVIIC or unlabelled GVIA for 30 min on ice, followed by the addition of $^{125}$I-MVIIC or $^{125}$I-GVIA. The mixture was then incubated at room temperature for 30 min. The amount of binding inhibited by the presence of unlabelled peptides was similarly measured by preincubating each with a specific amount of the unlabelled peptide. Following the room temperature incubation, the assay mixture was diluted with 2 ml of ice-cold wash medium containing 180 mM choline chloride, 20 mM HEPES/Tris (pH 7.4), 1.5 mM CaCl$_2$ and 1 mg/ml BSA. Membranes were collected on glass fiber filters (Whatman GF/C) under vacuum and washed three times with 2 ml of ice-cold wash medium. The amount of radioactivity on the filters was measured. In order to decrease nonspecific binding, 0.025% Tween 20 was included in the wash medium which was used both for washing, and for soaking the filters prior to membrane collection.

Example 6

Biological Activity of ω-Conotoxin Peptide MVIIC

All previously characterized ω-conotoxin peptides have been identified from crude venom by a dual symptomatology; the paralysis evoked in fish and the highly diagnostic "shaker" syndrome induced in mice upon IC injection of the toxins (6). As the dose injected into mice is increased, the shaking symptomatology generally becomes more intense, earlier in onset and longer in duration, but death does not occur.

The in vivo biological effects of MVIIC were assessed, and compared to the first characterized ω-conotoxin peptide from *C. magus* venom, ω-conotoxin peptide MVIIA and to the widely-used ω-conotoxin peptide GVIA. The data are shown in Table 1. All of the peptides are paralytic to fish at the doses tested. However, in mice, instead of the characteristic shaker syndrome, MVIIC causes a progressive decrease in respiration rate, with marked gasping for breath. The peptide was lethal at low doses (0.1–0.4 µg); in contrast, even at a 100-fold higher dose (40 µg), MVIIA did not cause lethality. Thus, the biological effects of ω-conotoxin peptides MVIIC and MVIIA are strikingly dissimilar in mice; the gasping/arched back syndrome and lethality are characteristic of MVIIC.

TABLE 1

Effects of ω-Conotoxin Peptides on Mice Upon Interacerebral Injection

| | ω-Conotoxin Peptide | |
|---|---|---|
| Dose (µg) | MVIIA | MVIIC |
| 0.04 | Shaking* | Back arched* |
| 0.10 | Shaking | Back arched after 30 min, comatose after 6 hr |
| 0.40 | Shaking | Gasping and back arched after 20 min, one of two mice dead after 40 min |
| 4.00 | Shaking | Respiratory depression after 15 min, death after 13 min |
| 40.00 | Shaking | Severe respiratory depression after 2 min, death in 12 min |

*(One of two mice).

Example 7

Effects of ω-Conotoxin Peptide MVIIC on Rat Hippocampal Pyramidal Neurons and Cerebellar Purkinje Neurons The effects of ω-conotoxin peptide MVIIC on isolated mammalian central neurons were assessed. Hippocampal pyramidal neurons from the CA1 region were used; these cells were of particular interest, since they have L- and N-currents (37, 38) as well as a significant fraction of Ca$^{2+}$ current which is insensitive to both dihydropyridines and ω-conotoxin peptide GVIA (39). The experimental results are shown in FIG. 2.

Figure 2A:
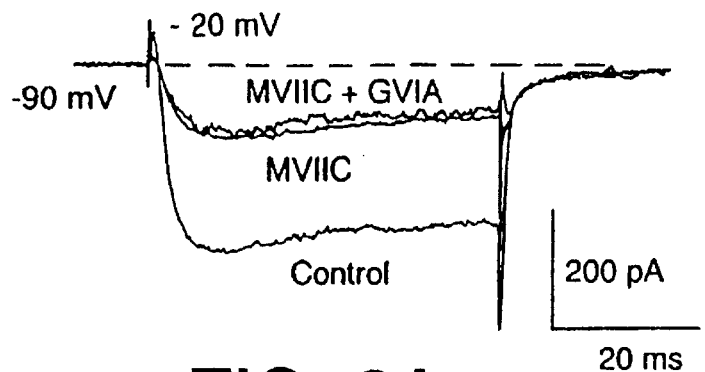
FIG. 2A shows partial block on $Ca^{2+}$ channels current in CA1 hippocampal neurons by ω-conotoxin peptide MVIIC and its occlusion of the block by ω-conotoxin peptide GVIA.
Figure 2B:
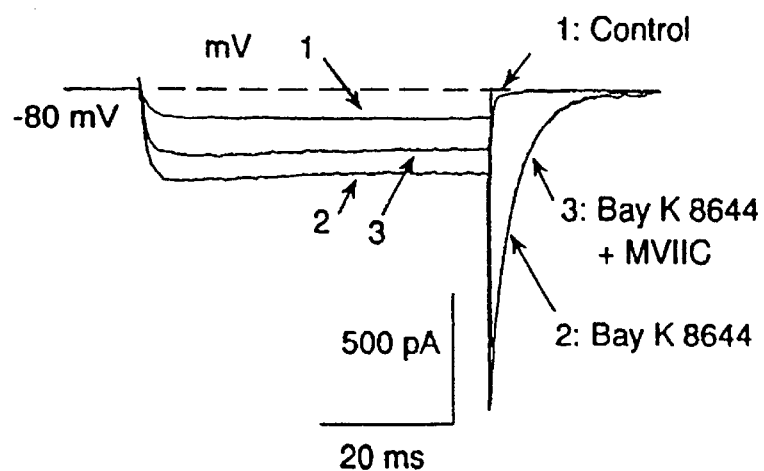
FIG. 2B shows the lack of effect of ω-conotoxin peptide MVIIC on L-type $Ca^{2+}$ channel current in CA1 hippocampal neurons.
Figure 2C:
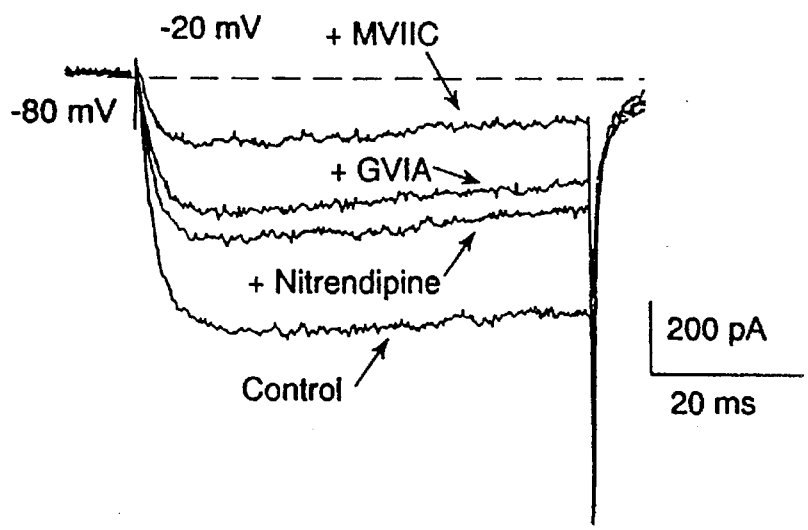
FIG. 2C shows that ω-conotoxin peptide MVIIC blocks a fraction of the non-L- and non-N-type $Ca^{2+}$ channel current in CA1 hippocampal neurons.

The experiment in FIG. 2A shows that the sequential addition of ω-conotoxin peptide GVIA to cells already inhibited by ω-conotoxin peptide MVIIC does not cause any further effect. Thus, MVIIC appears to inhibit all of the GVIA-sensitive Ca$^{2+}$ currents at the concentration used (10 µM). The experiment in FIG. 2B shows that the distinctive slow phase of the tail current induced by the dihydropyridine Bay K 8644 was unaffected by MVIIC. Thus, ω-conotoxin peptide MVIIC does not antagonize the L-currents in these cells up to at least 10 µM. The key experiment is shown in FIG. 2C, which demonstrates that a large fraction of the dihydropyridine-resistant, ω-conotoxin peptide GVIA-resistant current in the cells is inhibited by ω-conotoxin peptide MVIIC. Thus, these experiments reveal four pharmacologically distinguishable Ca$^{2+}$ currents in hippocampal CA1 pyramidal cells in culture. Ca$^{2+}$ currents can be either MVIIC-sensitive or -resistant. Furthermore, the MVIIC-sensitive currents can be divided into either GVIA sensitive (=N currents) or -resistant classes; the MVIIC-resistant currents are either dihydropyridine-sensitive (=L currents) or dihydropyridine-resistant.

Figure 3:
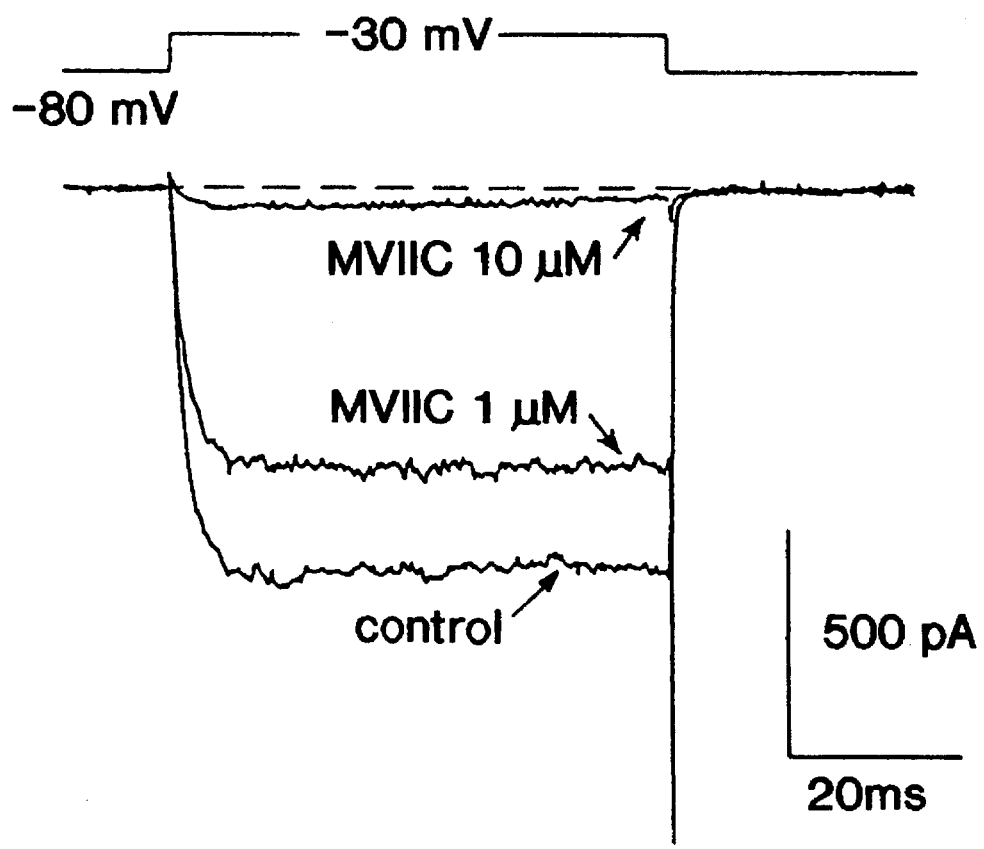
FIG. 3 shows the effect of ω-conotoxin peptide MVIIC on high-threshold $Ca^{2+}$ channel current in cerebellar Purkinje neuron.

The GVIA-insensitive, MVIIC-sensitive currents in the hippocampal neurons may include "P-like" currents. The prototypic "P" currents were first described in cerebellar Purkinje neurons (28, 29, 40). Ca$^{2+}$ currents in cerebellar Purkinje cells are inhibited by MVIIC (see FIG. 3) with an IC$_{50}$ between 1 µM and 10 µM under these conditions. However, the precise relationship of P-channels in Purkinje cells to the GVIA resistant, MVIIC sensitive channels in hippocampal neurons needs to be clarified by a more thorough pharmacological characterization. ω-Conotoxin peptide MVIIC is specific for voltage-sensitive $Ca^{2+}$ channels. When an excess of the toxin (10 μM) was applied to rat sympathetic neurons, no effects were observed on either $Na^+$ or $K^+$ currents in this cell (n=3 for $I_{Na}$, n=1 for IK).

Example 8

Effect of ω-Conotoxin Peptide MVIIC on Rat Brain Synaptosomes

ω-Conotoxin peptide GVIA is a potent inhibitor of depolarization-induced $^{45}Ca_{2+}$ uptake in chick brain synaptosomes, causing essentially complete inhibition (27). In contrast, in most experiments the major fraction of $^{45}Ca^{2+}$ entry in rat brain synaptosomes is not inhibited by ω-conotoxin peptide GVIA when a similar experimental protocol is used. The effects of ω-conotoxin peptide MVIIC on rat brain synaptosomes were examined, and the results compared to those with ω-conotoxin peptide GVIA. The results are shown in Table 2. In contrast to GVIA, MVIIC inhibits the major fraction of depolarization-induced $^{45}Ca^{2+}$ entry to rat brain synaptosomes at submicromolar concentrations.

TABLE 2

Rat Brain Synaptosomal Uptake of $^{45}Ca^{2+}$ in Absence or Presence of 2.5 μM Toxin

| Condition | Cpm | % Uptake* |
|---|---|---|
| High K$^+$ | 25,939 | 100 |
| | 26,026 | |
| Low K$^+$ | 6,153 | 0 |
| | 6,041 | |
| High K$^+$ + ω-conotoxin peptide GVIA | 25,780 | 99.5 |
| | 25,982 | |
| High K$^+$ × ω-conotoxin peptide GVIA | 11,107 | 26.9 |
| | 11,780 | |

*Rat brain synaptosomes were prepared as described in text. The difference between uptake in 71 mM K$^+$ ("high K$^+$") and 5 mM K$^+$ ("low K$^+$") when no toxin is present represents specific depolarization-induced influx of $^{45}Ca^{2+}$ and is defined as 100% uptake. Under same conditions, 2.5 μM ω-conotoxin peptide GVIA has no effect. Each condition was done in duplicate and values were averaged to calculate % uptake.

Example 9

Competition Binding Experiments with ω-Conotoxin MVIIC

In order to further define ω-conotoxin peptide MVIIC receptor sites, the peptide was labelled with $^{125}I$ and the moniodo-tyrosine derivative purified. Injection experiments with unlabelled $^{127}I$ ω-conotoxin peptide MVIIC had demonstrated that this analog is biologically active. The labeling procedure used was that previously described for preparing $^{125}I$-Tyr-MVIIA and GVIA derivatives (2).

A binding competition study of ω-conotoxin peptides GVIA, MVIIA and MVIIC with $^{125}I$ ω-conotoxin MVIIC using rat brain membranes was performed. The standard binding assays used conditions developed for GVIA assays; displacement of $^{125}I$-ω-conotoxin MVIIC by preincubation with different concentrations of unlabelled GVIA, MVIIA and MVIIC is dependent on the ionic strength. Under the standard low ionic strength conditions of Cruz and Olivera (2), a difference in affinity of two orders of magnitude between GVIA and MVIIA on the one hand, and MVIIC on the other, was seen, with the latter having the higher affinity. If the ionic strength in the assay was increased, GVIA and MVIIA failed to displace $^{125}I$-MVIIC; the apparent IC$_{50}$ difference is greater than four orders of magnitude (for MVIIC, ≈0.3 nM, for GVIA and MVIIA, >3 μM). In contrast, if radiolabelled ω-conotoxin peptide GVIA is used as the probe on rat brain membranes, the apparent affinities are reversed: GVIA and MVIIA exhibit higher affinity than MVIIC. Furthermore, the effects of ionic strength are not as dramatic; MVIIC has a respectable affinity (IC$_{50}$≈10 nM), even at the higher ionic strength. These results suggest that there are two distinct ω-conotoxin peptide sites in rat brain, and that the radiolabelled GVIA and MVIIC probes bind different sites under the experimental conditions used. The high affinity MVIIC site has a marked preference for MVIIC vs. GVIA and MVIIA at low ionic strength, with the affinity differences even more magnified under physiological conditions. These results help explain the dramatic in vivo differences observed in the effects of these toxins. The effects of MVIIC on $^{45}Ca^{2+}$ uptake by rat brain synaptosomes, and on $Ca^{2+}$ currents in cerebellar Purkinje cells are reminiscent of recently reported effects of a novel spider toxin, ω-agatoxin IVA, from the venom of the funnel web spider Agelenopsis aperta (29).

In order to assess whether MVIIC and ω-agatoxin IVA might be binding to the same high affinity sites, the ability of ω-agatoxin IVA to compete for high affinity $^{125}I$-ω-conotoxin peptide MVIIC binding to rat brain membrane sites was determined. The results of such a binding competition experiment are shown in Table 3. It is clear that, although all ω-conotoxin peptides can displace $^{125}I$-MVIIC under the conditions used, even relatively high concentrations of ω-agatoxin IVA do not compete for MVIIC binding.

TABLE 3

ω-Agatoxin IVA Does Not Compete With $^{125}I$-ω-Conotoxin Peptide MVIIC

| Assay* | Cps |
|---|---|
| Control (no additions) | 14,059 |
| + ω-Conotoxin Peptide MVIIC (100 nM) | 3,517 |
| + ω-Conotoxin Peptide MVIIC (500 nM) | 3,695 |
| + ω-Agatoxin IVA (0.1 nM) | 15,141 |
| + ω-Agatoxin IVA (0.3 nM) | 13,337 |
| + ω-Agatoxin IVA (4 nM) | 14,833 |
| + ω-Agatoxin IVA (100 nM) | 13,920 |
| + ω-Agatoxin IVA (500 nM) | 15,258 |

*Filter binding assays were performed using $^{125}I$-ω-conotoxin peptide MVIIC and rat synaptosomal membranes under standard conditions as described above. Under these conditions, the IC$_{50}$ of $^{125}I$-ω-conotoxin peptide MVIIC is ~0.3 nM and of ω-conotoxin peptides MVIIA and GVIA is ~30 nM.

Example 10

Biological Activity of ω-Conotoxin Peptide MVIID

The MVIID peptide synthesized as described above was assayed for biological activity using both fish and mice. As expected, the peptide caused paralysis and death in fish, a biological effect predicted of all ω-conotoxin peptides. Intramuscular injection of 0.2–0.4 nmol/g caused notable paralysis in goldfish within 30 seconds and death in 1–1.5 min.

The effects on mice were more complex. When injected intracranially into mice, doses between 0.1 to 2.0 nmol of the peptide elicited a variety of behaviors. At doses below 0.1 nmol, the animals appeared to be unaffected. However, between 0.1 and 0.2 nmol, the mice became hypersensitive to stimuli and jumped violently in response to being prodded. This behavior was observed transiently, typically within the first five minutes following injection. These short-term hypersensitivity symptoms were not observed with ω-conotoxin peptide GVIA. Later, the activity level of the mice characteristically decreased, and respiratory distress (as evidenced by slow, forced and difficult breathing) was observed after 7–12 minutes. Injections of 0.5 to 1 nmol caused no transient hyperactivity, but resulted in almost immediate lethargy, and in 5–7 minutes, extreme respiratory traum. Mice exhibited an arched back stance with head bowed low, mouth touching the floor. After about 12–20 minutes, they lay on their side with their hind legs kicking involuntarily and sporadically, with the whole body crunching while gasping for breath. No deaths occurred in mice injected with less than 0.2 nmol, one of two mice injected with 0.2 nmol died (1 hour, 15 minutes), and all mice injected with doses of 0.5 nmol or higher died within 40 minutes.

Example 11

Binding-Competition Experiments With ω-Conotoxin Peptide MVIID

Synthetic ω-conotoxin peptide MVIID was used in competition binding experiments with radiolabelled ω-conotoxin peptide GVIA, as well as ω-conotoxin peptide MVIIC. $^{125}$I-GVIA as the labelled probe and rat brain membranes as the source of the target $Ca^{2+}$ channels were used. The radiolabelled GVIA is displaced by unlabelled GVIA with subnanomolar affinity in agreement with previous studies. The affinity of MVIIC under these binding conditions is approximately 10-fold less ($K_D$ ca. $10^{-8}$ molar). The new peptide, MVIID, has an even lower affinity for the GVIA high affinity site.

In contrast, competition-displacement experiments using radiolabelled MVIIC demonstrate that ω-conotoxin peptides MCIIC and MVIID both have subnanomolar affinity for this site, while ω-conotoxin peptide GVIA has an affinity two orders of magnitude lower. The acetylcholine receptor-targeted peptide, ω-conotoxin peptide MI (41), does not compete for binding even when present in great excess. The results suggest that MVIID has approximately the same affinity for the high-affinity MVIIC site, but discriminates more against the ω-GVIA site than does MVIIC under these binding conditions.

Example 12

Effect of ω-Conotoxin peptide MVIID on Rat Brain Synaptosomes

Although N-type channels are believed to be present primarily at presynaptic termini in the mammalian CNS, this $Ca^{2+}$ channel subtype is not responsible for most voltage-activated $Ca^{2+}$ uptake under in vitro conditions. A standard in vitro assay is to depolarize synaptosomes and measure $^{45}Ca_{2+}$ an uptake; this is largely resistant to both dihydropyridine and ω-conotoxin peptide GVIA, indicating that the $Ca^{2+}$ channels which mediate voltage-sensitive $Ca^{2+}$ influx are neither of the L- nor N-type classes. The sensitivity of this $Ca^{2+}$ influx to ω-conotoxin peptide MVIID was tested. The sensitivity of $^{45}Ca^{2+}$ influx to ω-conotoxin peptides GVIA and MVIID is shown in Table 4. The results demonstrate that, although influx is largely insensitive to ω-conotoxin peptide GVIA, much of it is sensitive to MVIID, indicating that $Ca^{2+}$ channels which do not belong to the L-type and N-type classes are sensitive to ω-conotoxin peptide MVIID.

TABLE 4

$^{45}Ca^{2+}$ Influx Into Synaptosomes

| Uptake Conditions* | Radioactivity in Synaptosomes (cpm) | |
|---|---|---|
| | Experiment 1 (GVIA) | Experiment 2 (MVIID) |
| 5 mM K$^+$ Solution | 3,884 | 3,729 |
| | 3,926 | 4,236 |
| 71 mM K$^+$ Solution | 14,748 | 13,831 |
| | 14,226 | 14,382 |
| 71 mM K$^+$ Solution + ω-Conotoxin (2.5 μM) | 13,602 | 7,322 |
| | 12,207 | 7,732 |

*Uptake of $^{45}Ca^{2+}$ into rat brain synaptosomes was carried out as described in Hillyard et al. (30).

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES

1. Olivera, B. M. et al. (1984). Purification and sequence of a presynaptic peptide toxin from *Conus geographus* venom. *Biochemistry* 23:5087–90.
2. Cruz, L. J. et al. (1986). Calcium channel antagonists. *J. Biol. Chem.* 261:6230–33.
3. McCleskey, E. W. et al. (1987). Calcium channel blockade by a peptide from Conus: specificity and mechanism. *Proc. Nat. Acad. Sci. USA* 84:4327–31.
4. Yoshikami, D. et al. (1989). The inhibitory effects of omega-conotoxins on calcium channels and synapses. *Ann. N.Y. Acad. Sci.* 560:230–48.
5. Lundy, P. M. et al. (1991). Pharmacological evidence for an ω-conotoxin, dihydropridine-insensitive neuronal Ca channel. *Euro. J. Pharmacol.* 206:61–68.
6. Olivera, B. M. et al. (1985). Peptide neurotoxins from fish-hunting cone snails. *Science* 230:1338–43.
7. Olivera, B. M. et al. (1987). Neuronal calcium channel antaonists. Discrimination between calcium channel subtypes using ω-conotoxin from *Conus magus* venom. *Biochemistry* 26:2086–90.
8. Snutch, T. P., et al. (1990). Rat brain expresses a heterogeneous family of calcium channels. *Proc. Nat. Acad. Sci. USA* 87:3391–3395.
9. Mori, Y., et al. (1991). Primary structure and functional expression from complementary DNA of a brain calcium channel. *Nature* 350:398–402.
10. Snutch, T. P., et al. (1991). Distinct calcium channels are generated by alternative splicing and are differentially expressed in the mammalian CNS. *Neuron* 7:45–57.
11. Starr, T. V., et al. (1991). Primary structure of a calcium channel that is highly expressed in rat cerebellum. *Proc. Nat. Acad. Sci. USA* 88:5621–5625.
12. Olivera, B. M. et al. (1984). U.S. Pat. No. 4,447,356.
13. Sambrook, J. et al. (1979). *Molecular Cloning: A Laboratory Manual*, 2nd Ed., Cold Spring Harbor Laboratory, Cold Spring Harbor, N.Y.

LIST OF REFERENCES (Cont'd)

14. Gray, W. R. (1993). Multicyclic cysteine peptides: a new method for disulfide analysis. Abstract, 13th American Peptide Symposium, Edmonton, Alberta.

15. "Methoden der Organischen Chemie (Houben-Weyl): Synthese von Peptiden," E. Wunsch (Ed.), Georg Thieme Verlag, Stuttgart, Ger. (1974).
16. Stewart and Young, *Solid-Phase Peptide Synthesis*, Freeman & Co., San Francisco, Calif. (1969).
17. Vale et al. (1978). U.S. Pat. No. 4,105,603.
18. U.S. Pat. No. 3,972,859 (1976).
19. U.S. Pat. No. 3,842,067 (1974).
20. U.S. Pat. No. 3,862,925 (1975).
21. Bodansky et al. (1966). *Chem. Ind.* 38:1597–98.
22. U.S. Pat. No. 4,569,967.
23. Horiki, K. et al. (1978). *Chemistry Letters* 165–68.
24. Schroder & Lubke (1965). *The Peptides* 1:72–75, Academic Press, N.Y.
25. Kapoor (1970). *J. Pharm. Sci.* 59:1–27.
26. Kaiser et al. (1970). *Anal. Biochem.* 34:595.
27. Rivier J. R. et al. (1978). *Biopolymers* 17:1927–38.
28. Mintz, I. M. et al. (1992a). Block of P-type calcium channels by the funnel web spider toxin ω-Aga-IVA. *Nature* 355:827–29.
29. Llinas, R. et al. (1989). Blocking and isolation of a calcium channel from neurons in mammals and cephalopods utilizing a toxin fraction (FTX) from funnel-web spider poison. *Proc. Nat. Acad. Sci. USA* 86:1689–93.
30. Hillyard, D. R. et al. (1992). A new Conus peptide ligand for mammalian presynaptic Ca channels. *Neuron* 9:69–77.

LIST OF REFERENCES (Cont'd)

31. Rivier, J. R. et al. (1987). Neuronal calcium channel inhibitors: Synthesis of ω-conotoxin GVIA and effects on $^{45}$Ca-uptake by synaptosomes. *J. Biol. Chem.* 262:1194–98.
32. Veber, D. F. et al. (1972). Acetamidomethyl: a novel protecting group for cysteine. *J. Am. Chem. Soc.* 94:5456–61.
33. Kamber, B. et al. (1980). The synthesis of cysteine peptides by iodine oxidation of S-trityl cysteine and S-acetamidomethyl-cysteine peptides, *Helv. Chim. Acta* 63:899–915.
34. Ramilo, C. A. et al. (1992). Novel α- and ω-conotoxins from *Conus striatus* venom. *Biochemistry* 31:9919–26.
35. Burns, J. A. et al. (1991). Selective reduction of disulfides by tris-[2-carboxyethyl]-phosphine. *J. Organ. Chem.* 56:2648–50.
36. Hamill, O. P. et al. (1981). Improved patch clamp techniques for high-resolution current reading from cells and cell-free membrane patches. *Plfgers Arch.* 391:85–100.
37. Mogul, D. J. et al. (1991). Evidence for multiple types of $Ca^{2+}$ channels in acutely isolated hippocampal CA3 neutons of the guinea pig. *J.Physiol.* (Lond.) 433:259–81.
38. O'Dell, T. J. et al. (1991). Single calcium channels in rat and guinea-pig hippocampal neurons. *J. Physiol.* (Lond.) 436:739–67.
39. Regan, L. J. et al. (1991). $Ca^{2+}$ channels in rat central and peripheral neurons: high-threshold current resistant to dihydropyridine blockers and ω-conotoxin. *Neuron* 6:269–80.
40. Regan, L. J. (1991). Voltage-dependent calcium currents in Purkinje cells from rat cerebellar vermis. *J. Neurosci.* 11:2259–2269.
41. Mcintosh, M. et al. (1982). Isolation and structure of a peptide toxin from the marine snail *Conus magus*. *Arch. Biochem. Biophys.* 218:329–334.

---

What is claimed is:

1. A substantially pure ω-conotoxin peptide having the formula Cys-Xaa$_1$-Gly-Xaa$_2$-Gly-Ala-Xaa$_3$-Cys-Arg-Lys-Thr-Xaa$_4$-Tyr-Xaa$_5$-Cys-Cys-Ser-Gly-Ser-Cys-Xaa$_6$-Arg-Gly-Xaa$_7$-Cys (SEQ ID NO:2), wherein Xaa$_1$ is Lys or Gln, Xaa$_2$ is Lys or Arg, Xaa$_3$ is Pro, Ser or 4-hydroxyproline, Xaa$_4$ is Met, Ser or norleucine, Xaa$_5$ is Asp or Asn, Xaa$_6$ is Gly-Arg or Asn and Xaa$_7$ is Lys or Arg.

2. The peptide of claim 1 wherein the C-terminus is amidated.

3. A substantially pure ω-conotoxin peptide having the formula Cys-Lys-Gly-Lys-Gly-Ala-Xaa$_1$-Cys-Arg-Lys-Thr-Xaa$_2$-Tyr-Asp-Cys-Cys-Ser-Gly-Ser-Cys-Gly-Arg-Arg-Gly-Lys-Cys (SEQ ID NO:3), wherein Xaa$_1$ is Pro or 4-hydroxyproline and Xaa$_2$ is Met or norleucine.

4. The peptide of claim 3 wherein Xaa$_2$ is Met.

5. The peptide of claim 4 wherein Xaa$_1$ is Pro.

6. The peptide of claim 3 wherein Xaa$_2$ is norleucine.

7. The peptide of claim 3 wherein the C-terminus is amidated.

8. The peptide of claim 4 wherein the C-terminus is amidated.

9. The peptide of claim 5 wherein the C-terminus is amidated.

10. The peptide of claim 6 wherein the C-terminus is amidated.

11. The peptide of claim 5 wherein Xaa$_2$ is norleucine.

12. The peptide of claim 3 wherein Xaa$_1$ is Pro.

13. The peptide of claim 11 wherein the C-terminus is amidated.

14. The peptide of claim 12 wherein the C-terminus is amidated.

15. A substantially pure ω-conotoxin peptide having the formula Cys-Gln-Gly-Arg-Gly-Ala-Ser-Cys-Arg-Lys-Thr-Xaa-Tyr-Asn-Cys-Cys-Ser-Gly-Ser-Cys-Asn-Arg-Gly-Arg-Cys (SEQ ID NO:4), wherein Xaa is Met or norleucine.

16. The peptide of claim 15 wherein Xaa is Met.

17. The peptide of claim 15 wherein Xaa is norleucine.

18. The peptide of claim 15 wherein the C-terminus is amidated.

19. The peptide of claim 16 wherein the C-terminus is amidated.

20. The peptide of claim 17 wherein the C-terminus is amidated.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 13 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
        ( A ) ORGANISM: Conus magus ( x i ) SEQUENCE DESCRIPTION: SEQ ID NO:1:

Cys Arg Lys Thr Xaa Tyr Xaa Cys Cys Ser Gly Ser Cys
1               5               10

( 2 ) INFORMATION FOR SEQ ID NO:2:

( i ) SEQUENCE CHARACTERISTICS:
        ( A ) LENGTH: 25 amino acids
        ( B ) TYPE: amino acid (C) STRANDEDNESS: single
(D) TOPOLOGY: linear (ii) MOLECULE TYPE: peptide (iii) HYPOTHETICAL: NO (iv) ANTI-SENSE: NO (vi) ORIGINAL SOURCE:
  (A) ORGANISM: Conus magus (xi) SEQUENCE DESCRIPTION: SEQ ID NO:2:

```
Cys Xaa Gly Xaa Gly Ala Xaa Cys Arg Lys Thr Xaa Tyr Xaa Cys Cys
1               5                   10                  15
Ser Gly Ser Cys Xaa Arg Gly Xaa Cys
            20              25
```

(2) INFORMATION FOR SEQ ID NO:3:

(i) SEQUENCE CHARACTERISTICS:
    (A) LENGTH: 26 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (vi) ORIGINAL SOURCE:
    (A) ORGANISM: Conus magus (ix) FEATURE:
    (A) NAME/KEY: Disulfide-bond
    (B) LOCATION: 1..16

(ix) FEATURE:
    (A) NAME/KEY: Disulfide-bond
    (B) LOCATION: 8..20

(ix) FEATURE:
    (A) NAME/KEY: Disulfide-bond
    (B) LOCATION: 15..26

(ix) FEATURE:
    (A) NAME/KEY: Modified-site
    (B) LOCATION: 7..8
    (D) OTHER INFORMATION: /note="Xaa at residue 7 is Pro or
        4- hydroxyPro"

(ix) FEATURE:
    (A) NAME/KEY: Modified-site
    (B) LOCATION: 12..13
    (D) OTHER INFORMATION: /note="Xaa at residue 12 is Met or
        norleucine"

(xi) SEQUENCE DESCRIPTION: SEQ ID NO:3:

```
Cys Lys Gly Lys Gly Ala Xaa Cys Arg Lys Thr Xaa Tyr Asp Cys Cys
1               5                   10                  15
Ser Gly Ser Cys Gly Arg Arg Gly Lys Cys
            20              25
```

(2) INFORMATION FOR SEQ ID NO:4:

(i) SEQUENCE CHARACTERISTICS:
    (A) LENGTH: 25 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (vi) ORIGINAL SOURCE:
                (A) ORGANISM: Conus magus (ix) FEATURE:
                (A) NAME/KEY: Disulfide-bond
                (B) LOCATION: 1..16

(ix) FEATURE:
                (A) NAME/KEY: Disulfide-bond
                (B) LOCATION: 8..20

(ix) FEATURE:
                (A) NAME/KEY: Disulfide-bond
                (B) LOCATION: 15..25

(ix) FEATURE:
                (A) NAME/KEY: Modified-site
                (B) LOCATION: 12..13
                (D) OTHER INFORMATION: /note="Xaa at residue 12 is Met or
                        norleucine"

(xi) SEQUENCE DESCRIPTION: SEQ ID NO:4:

Cys Gln Gly Arg Gly Ala Ser Cys Arg Lys Thr Xaa Tyr Asn Cys Cys
        1               5                   10                  15

Ser Gly Ser Cys Asn Arg Gly Arg Cys
                    20                  25

(2) INFORMATION FOR SEQ ID NO:5:

(i) SEQUENCE CHARACTERISTICS:
                (A) LENGTH: 17 base pairs
                (B) TYPE: nucleic acid
                (C) STRANDEDNESS: single
                (D) TOPOLOGY: linear (ii) MOLECULE TYPE: cDNA (iii) HYPOTHETICAL: YES (iv) ANTI-SENSE: NO (vi) ORIGINAL SOURCE:
                (A) ORGANISM: Conus magus (xi) SEQUENCE DESCRIPTION: SEQ ID NO:5:

GTRCARCART CRTACAT           17

(2) INFORMATION FOR SEQ ID NO:6:

(i) SEQUENCE CHARACTERISTICS:
                (A) LENGTH: 6 amino acids
                (B) TYPE: amino acid
                (C) STRANDEDNESS: single
                (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
                (A) ORGANISM: Conus magus (xi) SEQUENCE DESCRIPTION: SEQ ID NO:6:

Met Tyr Asp Cys Cys Thr
        1               5

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Conus magus (xi) SEQUENCE DESCRIPTION: SEQ ID NO:7:

```
GAAGTCCTAT GACATGA                                                17
```

(2) INFORMATION FOR SEQ ID NO:8:

(i) SEQUENCE CHARACTERISTICS:
        (A) LENGTH: 90 base pairs
        (B) TYPE: nucleic acid
        (C) STRANDEDNESS: single
        (D) TOPOLOGY: linear (ii) MOLECULE TYPE: peptide (iii) HYPOTHETICAL: NO (iv) ANTI-SENSE: NO (vi) ORIGINAL SOURCE:
        (A) ORGANISM: Conus magus (ix) FEATURE:
        (A) NAME/KEY: CDS
        (B) LOCATION: 1..87

(xi) SEQUENCE DESCRIPTION: SEQ ID NO:8:

```
ACT  CGC  TGC  AAG  GGT  AAA  GGA  GCA  CCA  TGT  CGT  AAG  ACT  ATG  TAT  GAC       48
Thr  Arg  Cys  Lys  Gly  Lys  Gly  Ala  Pro  Cys  Arg  Lys  Thr  Met  Tyr  Asp
1                   5                        10                       15

TGC  TGC  AGC  GGT  TCT  TGC  GGC  AGG  AGA  GGT  AAA  TGT  GGC  TGA                 90
Cys  Cys  Ser  Gly  Ser  Cys  Gly  Arg  Arg  Gly  Lys  Cys  Gly
                    20                       25
```

(2) INFORMATION FOR SEQ ID NO:9:

(i) SEQUENCE CHARACTERISTICS:
        (A) LENGTH: 29 amino acids
        (B) TYPE: amino acid
        (D) TOPOLOGY: linear (ii) MOLECULE TYPE: protein (xi) SEQUENCE DESCRIPTION: SEQ ID NO:9:

```
Thr  Arg  Cys  Lys  Gly  Lys  Gly  Ala  Pro  Cys  Arg  Lys  Thr  Met  Tyr  Asp
1                   5                        10                       15

Cys  Cys  Ser  Gly  Ser  Cys  Gly  Arg  Arg  Gly  Lys  Cys  Gly
                    20                       25
```

(2) INFORMATION FOR SEQ ID NO:10:

(i) SEQUENCE CHARACTERISTICS:
        (A) LENGTH: 17 base pairs
        (B) TYPE: nucleic acid
        (C) STRANDEDNESS: single (D) TOPOLOGY: linear (ii) MOLECULE TYPE: cDNA (iii) HYPOTHETICAL: NO (iv) ANTI-SENSE: NO (vi) ORIGINAL SOURCE:
    (A) ORGANISM: Conus magus (xi) SEQUENCE DESCRIPTION: SEQ ID NO:10:

CCATGTCGTA AGACTAT                    17

(2) INFORMATION FOR SEQ ID NO:11:

(i) SEQUENCE CHARACTERISTICS:
    (A) LENGTH: 6 amino acids
    (B) TYPE: amino acid
    (C) STRANDEDNESS: single
    (D) TOPOLOGY: linear (ii) MOLECULE TYPE: peptide (iii) HYPOTHETICAL: NO (iv) ANTI-SENSE: NO (v) FRAGMENT TYPE: internal (vi) ORIGINAL SOURCE:
    (A) ORGANISM: Conus magus (xi) SEQUENCE DESCRIPTION: SEQ ID NO:11:

Pro  Cys  Arg  Lys  Thr  Met
1                5

(2) INFORMATION FOR SEQ ID NO:12:

(i) SEQUENCE CHARACTERISTICS:
    (A) LENGTH: 90 base pairs
    (B) TYPE: nucleic acid
    (C) STRANDEDNESS: single
    (D) TOPOLOGY: linear (ii) MOLECULE TYPE: cDNA (iii) HYPOTHETICAL: NO (iv) ANTI-SENSE: NO (vi) ORIGINAL SOURCE:
    (A) ORGANISM: Conus magus (ix) FEATURE:
    (A) NAME/KEY: CDS
    (B) LOCATION: 1..87

(xi) SEQUENCE DESCRIPTION: SEQ ID NO:12:

TCG  ACT  CGC  TGC  CAG  GGT  AGA  GGA  GCA  TCA  TGT  CGT  AAG  ACT  ATG  TAT    48
Ser  Thr  Arg  Cys  Gln  Gly  Arg  Gly  Ala  Ser  Cys  Arg  Lys  Thr  Met  Tyr
1                   5                        10                       15

AAC  TGC  TGC  AGC  GGT  TCT  TGC  AAC  AGA  GGT  AGA  TGT  GGC  TGA              90
Asn  Cys  Cys  Ser  Gly  Ser  Cys  Asn  Arg  Gly  Arg  Cys  Gly
                     20                        25

(2) INFORMATION FOR SEQ ID NO:13:

(i) SEQUENCE CHARACTERISTICS:
    (A) LENGTH: 29 amino acids
    (B) TYPE: amino acid
    (D) TOPOLOGY: linear (i i) MOLECULE TYPE: protein (x i) SEQUENCE DESCRIPTION: SEQ ID NO:13:

Ser Thr Arg Cys Gln Gly Arg Gly Ala Ser Cys Arg Lys Thr Met Tyr
1               5                   10                  15
Asn Cys Cys Ser Gly Ser Cys Asn Arg Gly Arg Cys Gly
            20                  25